US012678286B2

(12) United States Patent
    Shimko

(10) Patent No.:    US 12,678,286 B2
(45) Date of Patent:        Jul. 14, 2026

(54) IMPLANTABLE COMPOSITIONS HAVING FIBERS AND METHODS OF MAKING AND USING THEM

(71) Applicant: Warsaw Orthopedic, Inc., Warsaw, IN (US)

(72) Inventor: Daniel A. Shimko, Germantown, TN (US)

(73) Assignee: Warsaw Orthopedic, Inc., Warsaw, IN (US)

( * ) Notice:     Subject to any disclaimer, the term of this patent is extended or adjusted under 35 U.S.C. 154(b) by 969 days.

(21) Appl. No.: 17/892,459

(22) Filed:     Aug. 22, 2022

(65)             Prior Publication Data

US 2022/0395373 A1     Dec. 15, 2022

Related U.S. Application Data

(62) Division of application No. 16/518,216, filed on Jul. 22, 2019, now Pat. No. 11,426,280.

(51) Int. Cl.
    *A61F 2/28*         (2006.01)
    *A61F 2/30*         (2006.01)
              (Continued)

(52) U.S. Cl.
    CPC ........... *A61F 2/28* (2013.01); *A61F 2/30942* (2013.01); *B29C 64/393* (2017.08); *B33Y 50/02* (2014.12); *B33Y 70/00* (2014.12); *B33Y 70/10* (2020.01); *B33Y 80/00* (2014.12); *A61F 2002/2835* (2013.01); *A61F 2002/30062* (2013.01); *A61F 2002/30677* (2013.01); *A61F 2002/30943* (2013.01); *A61F 2002/30952*

(2013.01); *A61F 2002/30985* (2013.01); *A61F 2310/00359* (2013.01); *B29L 2031/7532* (2013.01)

(58) Field of Classification Search
    CPC ................................ A61F 2/28; A61F 2/4644
    See application file for complete search history.

(56)             References Cited

U.S. PATENT DOCUMENTS 9,034,358 B2    5/2015  Behnam et al.
    9,410,267 B2    8/2016  Parker et al.
              (Continued)

FOREIGN PATENT DOCUMENTS

EP          1638621 B1     3/2016
    KR    10-2012-0099058 A     9/2012

OTHER PUBLICATIONS

China Office Action. China Patent Office. China Application No. 202080063208.1. Apr. 17, 2025.
              (Continued)

*Primary Examiner* — Brian A Dukert
(74) *Attorney, Agent, or Firm* — Sorell, Lenna & Schmidt, LLP

(57)             ABSTRACT

An implantable composition, method of making and using the implantable composition is provided. The implantable composition comprising a first set of fibers and a second set of fibers, the first set of fibers manufactured to have a first binding surface, the second set of fibers manufactured to have a second binding surface, the first binding surface of the first set of fibers configured to bind at least at or near the second binding surface of the second set of fibers and the second set of fibers configured to bind at least at or near the first binding surface of the first set of fibers.

18 Claims, 17 Drawing Sheets

(51) Int. Cl.

| | |
|---|---|
| *B29C 64/393* | (2017.01) |
| *B33Y 50/02* | (2015.01) |
| *B33Y 70/00* | (2020.01) |
| *B33Y 70/10* | (2020.01) |
| *B33Y 80/00* | (2015.01) |
| B29L 31/00 | (2006.01) |

(56) References Cited

U.S. PATENT DOCUMENTS

| | | | |
|---|---|---|---|
| 10,071,120 | B2 | 9/2018 | Drapeau et al. |
| 10,173,375 | B2 | 1/2019 | Meyer et al. |
| 11,338,061 | B2 | 5/2022 | Bagga et al. |
| 2003/0039676 | A1 | 2/2003 | Boyce et al. |
| 2013/0189338 | A1 | 7/2013 | Drapeau et al. |
| 2015/0037385 | A1 | 2/2015 | Shah et al. |
| 2015/0374450 | A1 | 12/2015 | Mansfield et al. |
| 2016/0135954 | A1 | 5/2016 | Schlachter et al. |
| 2016/0136329 | A1 | 5/2016 | Schlachter et al. |
| 2016/0166303 | A1 | 6/2016 | Schlachter et al. |
| 2017/0312079 | A1* | 11/2017 | Schlachter ............. A61L 27/54 |
| 2018/0296343 | A1 | 10/2018 | Wei |
| 2018/0303616 | A1 | 10/2018 | Bhattacharyya et al. |
| 2018/0353299 | A1 | 12/2018 | Wei |

OTHER PUBLICATIONS

European Search Report for EP 20844537.9 date of completion is Jun. 20, 2023 (7 pages).

International Search Report for PCT/US2020/042355 date of completion is Nov. 6, 2020 (5 pages).

Bose, S., et al. "Bone Tissue Engineering Using 3D Printing" Materials Today, vol. 16, No. 12, Dec. 2013, pp. 496-504.

European Office Action. European Patent Office. European Application No. 20 844 537.9-1122. Mar. 10, 2025.

Notice of Second China Office Action. China Patent Office. China Application No. 202080063208.1. Oct. 30, 2025. 13 pages.

* cited by examiner

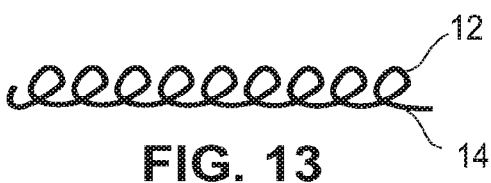
FIG. 13
FIG. 14
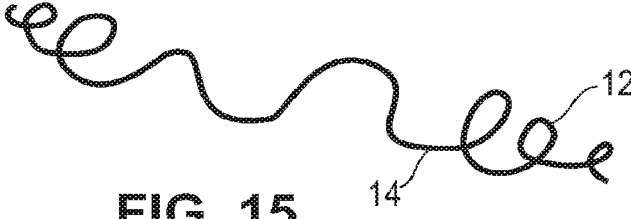
FIG. 15
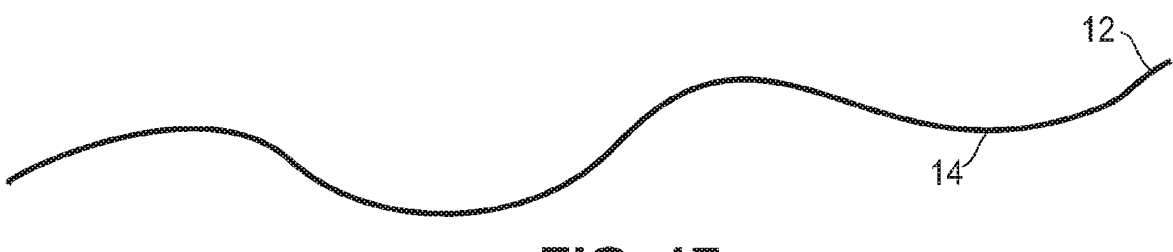
FIG. 16
FIG. 17

1000

INPUT INSTRUCTIONS
FOR CONTROLLER
1002

ALIGN PRINTING SURFACE
BASE AND APPLICATOR
1004

APPLICATOR DEPOSITS MATERIAL
ONTO PRINTING SURFACE
1006

MOVING PRINTING SURFACE AND
MOVE BASE TO CREATE PATTERN OF
FIBER HAVING BINDING AND
NON-BINDING SURFACE
1008

MATERIAL IS SOLIDIFIED
ON PRINTING SURFACE
1010

REMOVING THE FIBER FROM
THE PRINTING SURFACE
1012

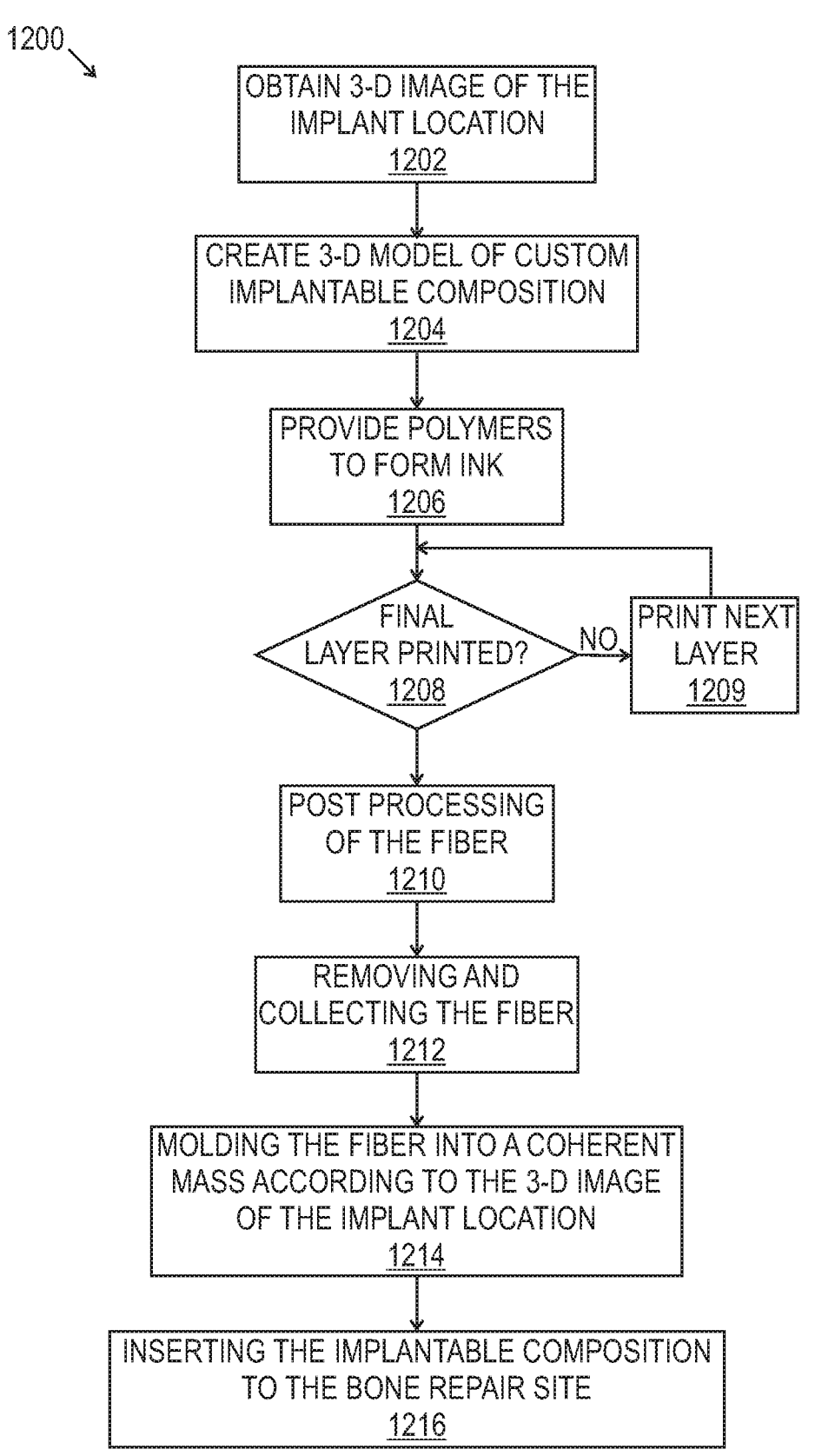

1200

OBTAIN 3-D IMAGE OF THE
IMPLANT LOCATION
1202

CREATE 3-D MODEL OF CUSTOM
IMPLANTABLE COMPOSITION
1204

PROVIDE POLYMERS
TO FORM INK
1206

FINAL
LAYER PRINTED?
1208

NO

PRINT NEXT
LAYER
1209

POST PROCESSING
OF THE FIBER
1210

REMOVING AND
COLLECTING THE FIBER
1212

MOLDING THE FIBER INTO A COHERENT
MASS ACCORDING TO THE 3-D IMAGE
OF THE IMPLANT LOCATION
1214

INSERTING THE IMPLANTABLE COMPOSITION
TO THE BONE REPAIR SITE
1216

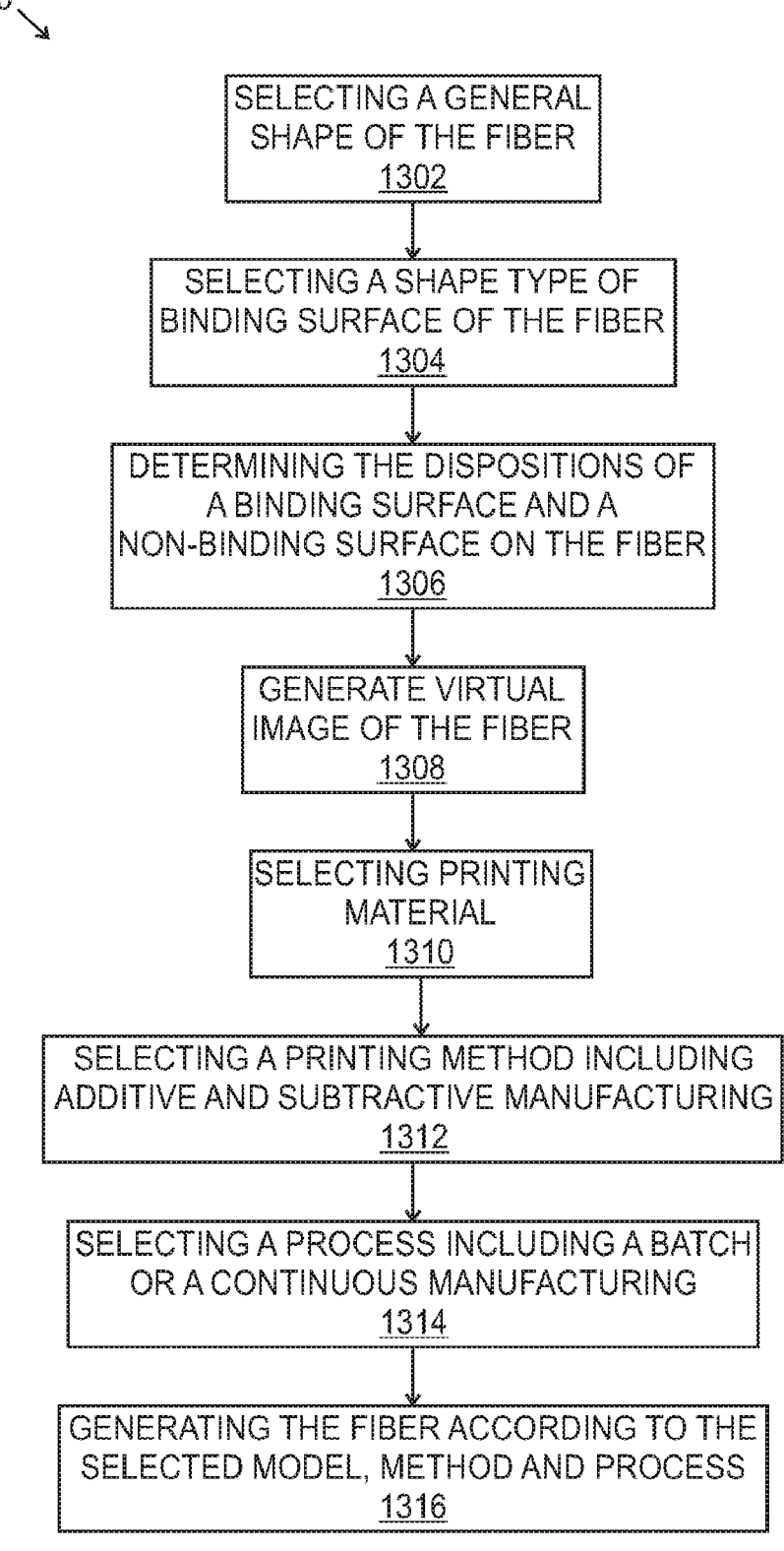

SELECTING A GENERAL
SHAPE OF THE FIBER
1302

SELECTING A SHAPE TYPE OF
BINDING SURFACE OF THE FIBER
1304

DETERMINING THE DISPOSITIONS OF
A BINDING SURFACE AND A
NON-BINDING SURFACE ON THE FIBER
1306

GENERATE VIRTUAL
IMAGE OF THE FIBER
1308

SELECTING PRINTING
MATERIAL
1310

SELECTING A PRINTING METHOD INCLUDING
ADDITIVE AND SUBTRACTIVE MANUFACTURING
1312

SELECTING A PROCESS INCLUDING A BATCH
OR A CONTINUOUS MANUFACTURING
1314

GENERATING THE FIBER ACCORDING TO THE
SELECTED MODEL, METHOD AND PROCESS
1316

FIG. 34

IMPLANTABLE COMPOSITIONS HAVING FIBERS AND METHODS OF MAKING AND USING THEM

BACKGROUND

It is estimated that more than half a million bone grafting procedures are performed in the United States annually with a cost over $2.5 billion. These numbers are expected to double by 2020. Both natural bone and bone substitutes have been used as graft materials. Natural bone may be autograft or allograft. Bone substitutes include natural or synthetic materials such as collagen, silicone, acrylics, calcium phosphate, calcium sulfate, or the like.

There are at least three ways in which a bone graft can help repair a defect. The first is osteogenesis, the formation of new bone within the graft by the presence of bone-forming cells called osteoprogenitor cells. The second is osteoinduction, a process in which molecules contained within the graft (e.g., bone morphogenetic proteins and other growth factors) convert progenitor cells into bone-forming cells. The third is osteoconduction, a physical effect by which a matrix often containing graft material acts as a scaffold on which bone and cells in the recipient are able to form. The scaffolds promote the migration, proliferation and differentiation of bone cells for bone regeneration.

Bone fiber based-demineralized bone matrices for implantation exhibit improvements in mechanical properties, including fiber length, fiber diameter or width, fiber aspect ratio, or a combination of multiple variables.

However, in making demineralized bone matrix (DBM) fibers, there is limited supply due to the limited availability of donor bone and at this time regulations do not permit the pooling of donor bone material. Further, during the manufacture of DBM fibers there is bone material that is not in fiber form but rather particles. Typically, these DBM particles possess random, irregular geometries with bone particles size ranging from about 110 to 850 microns and are usually wasted.

There is a need for implantable compositions and methods that are in fiber form that, in some embodiments, allow osteogenesis, osteoinduction and/or osteoconduction. These fibers can be manufactured to bind together and form an implant that can be used to treat, among other things, a bone defect.

SUMMARY

The present disclosure provides implantable compositions and methods that are in fiber form that, in some embodiments, allow osteogenesis, osteoinduction and/or osteoconduction. These fibers can be manufactured to bind together and form an implant that can be used to treat, among other things, a bone defect.

In some embodiments, an implantable composition is provided. The implantable composition comprises a first set of fibers and a second set of fibers, the first set of fibers comprising a first binding surface, the second set of fibers comprising a second binding surface, the first binding surface of the first set of fibers configured to bind at least at or near the second binding surface of the second set of fibers and the second set of fibers configured to bind at least at or near the first binding surface of the first set of fibers.

According to other aspects, provided is a computer implemented method for producing an implantable composition, the method comprising generating a 3-D digital model of the implantable composition, the 3-D digital model being of a first set of fibers and a second set of fibers, the first set of fibers comprising a first binding surface and a first non-binding surface, the second set of fibers comprising a second binding surface and a second non-binding surface, the first binding surface of the first set of fibers configured to bind at least at or near the second binding surface of the second set of fibers and the second set of fibers configured to bind at least at or near the first binding surface of the first set of fibers; and storing the 3-D digital model on a database coupled to a processor, the processor having instructions for selecting the implant material based on the stored 3-D digital model and for instructing a print surface of a 3-D printer to print the implantable composition on the print surface.

According to other embodiments, provided is a method of treating a bone or soft tissue defect, the method comprising inserting an implantable composition into the bone or soft tissue defect, the implantable composition comprising a first set of fibers and a second set of fibers, the first set of fibers comprising a first binding surface and a first non-binding surface, the second set of fibers comprising a second binding surface and a second non-binding surface, the first binding surface of the first set of fibers bound to at least at or near the second binding surface of the second set of fibers and the second set of fibers bound to at least at or near the first binding surface of the first set of fibers.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent regarding the following description, appended claims and accompanying drawings.

FIG. 13 illustrates an embodiment of a top view of an exemplary fiber having a binding surface and a non-binding surface.

FIG. 14 illustrates an embodiment of a top view of an exemplary fiber having a binding surface and a non-binding surface.

FIG. 15 illustrates an embodiment of a top view of an exemplary fiber having a binding surface and a non-binding surface.

FIG. 16 illustrates an embodiment of a top view of an exemplary fiber having a binding surface and a non-binding surface.

FIG. 17 illustrates an embodiment of a top view of an exemplary fiber having a binding surface and a non-binding surface.

FIG. 33 is a flow diagram illustrating representative steps that the logic performs of the computer-implemented system for producing a fiber of an implantable composition according to an embodiment of this application.

FIG. 34 is a flow diagram illustrating representative steps that the logic performs of the computer-implemented system for producing a fiber of an implantable composition according to an embodiment of this application.

Figure 1:
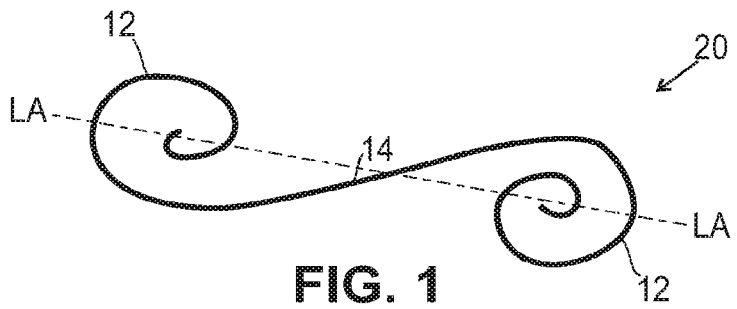
FIG. 1 illustrates an embodiment of a top view of an exemplary fiber having a binding surface and a non-binding surface.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Allograft, as used herein, refers to a graft of tissue obtained from a donor of the same species as, but with a different genetic make-up from the recipient, as a tissue transplant between two humans.

The implantable composition can have a bioactive agent disposed in or on the fiber. Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, clonidine, a statin, bone morphogenetic protein, anti-angiogenic factors, angiogenic factors, anti-secretory factors, anticoagulants and/or antithrombotic agents, local anesthetics, prostaglandins, anti-depressants, anti-psychotic substances, anti-emetics, and imaging agents. In certain embodiments, the bioactive agent can be includes nutraceuticals such as ascorbic acid, zinc, calcium, vitamin, garcinia cambogia, Omega 3 Fatty Acids, Alpha-lipoic Acid or a combination thereof. In another embodiment, the bioactive agent can be cell growth promoters such as sugar or a combination thereof. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD.

A binding surface includes a surface on a portion of a fiber that is designed to mechanically bind or entangle with another fiber.

A non-binding surface includes a surface on a portion of a fiber that is designed not to mechanically bind or entangle with another fiber if it contacts another non-binding surface. For example, if a linear surface contacts another fiber that has a linear surface, the two fibers will not mechanically entangle. However, if a non-binding surface of one fiber contacts a binding surface of another fiber, for example, a liner portion of one fiber contacts a hooked portion of another fiber, there will be binding or mechanical entanglement.

Biocompatible, as used herein, is intended to describe fibers that, upon administration in vivo, do not induce undesirable long-term effects.

Biodegradable includes fibers that will degrade over time by the action of enzymes, by hydrolytic action, oxidative action, and/or by other similar mechanisms in the human body. In various embodiments, "biodegradable" includes that components can break down or degrade within the body to non-toxic components as cells (e.g., bone cells) infiltrate the components and allow repair of the defect. By "biodegradable" it is meant that the fiber will erode or degrade over time due, at least in part, to contact with substances found in the surrounding tissue, fluids or by cellular action. By "bioabsorbable" it is meant that the fiber will be broken down and absorbed within the human body, for example, by a cell or tissue. "Biocompatible" means that the fiber will not cause substantial tissue irritation or necrosis at the target tissue site and/or will not be carcinogenic.

Bone, as used herein, refers to bone that is cortical, cancellous or cortico-cancellous of autogenous, allogenic, xenogenic, or transgenic origin. In some embodiments, the fiber can have bone material disposed in or on the fiber.

Bone graft, as used herein, refers to any implant prepared in accordance with the embodiments described herein and therefore may include expressions such as bone material and bone membrane.

The implant can include ceramic scaffolding. Ceramic scaffolding, as used herein, refers to implant scaffolding that comprises ceramic materials such as calcium phosphate ceramics or silicon ceramic, calcium-silicate-based bioglass, silicon calcium phosphate, tricalcium phosphate (TCP) and other ceramic or synthetic ceramic material described hereinafter.

Demineralized, as used herein, refers to any material generated by removing mineral material from tissue, for example, bone tissue. In certain embodiments, demineralized bone material may be added to the fiber. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 70%, 25%, 30%, 35%, 40%, 45%, 50%, 55%, 60%, 65%, 70%, 75%, 80%, 85%, 90%, 95%, 96%, 97%, 98% or of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or the entire surface of the bone can be demineralized. For example, part or the entire surface of the bone material can be demineralized to a depth of from about 100 to about 5000 microns, or about 150 microns to about 1000 microns.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

The fiber may be used as an osteoimplant. Osteoimplant refers to any device or material for implantation that aids or augments bone formation or healing. An osteoimplant may include any material, such as allograft, xenograft, or synthetic material, used to promote or support bone healing. The osteoimplant may be homogeneous or heterogeneous. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, oral and maxillofacial surgical procedures such as the repair of simple and compound fractures and non-unions, external, and internal fixations, joint reconstructions such as arthrodesis, general arthroplasty, deficit filling, disectomy, laminectomy, anterior cervical and thoracic operations, or spinal fusions.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as a bone tumor. DBM has been shown to promote bone formation in vivo by osteoconductive and osteoinductive processes. The osteoinductive effect of implanted DBM compositions results from the presence of active growth factors present on the isolated collagen-based matrix. These factors include members of the TGF-R, IGF, and BMP protein families. Particular examples of osteoinductive factors include TGF-$\beta$, IGF-1, IGF-2, BMP-2, BMP-7, parathyroid hormone (PTH), and angiogenic factors, Other osteoinductive factors such as osteocalcin and osteopontin are also likely to be present in DBM preparations as well. There are also likely to be other unnamed or undiscovered osteoinductive factors present in DBM.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the fibers of the present application means the ratio of the longest average dimension of the fiber (average length) to its shortest average dimension (average thickness). This is also referred to as the "aspect ratio" of the fiber.

Fibers, in some embodiments, can have an average length to average thickness ratio or aspect ratio from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibers can be described as filaments, threads, narrow strips, or thin sheets. Often, where thin sheets are produced, their edges tend to curl up toward each other. The fibers can have linear portions, which are often non-binding surfaces or they can be coiled to resemble springs, which are often the binding surfaces that allow binding with other fibers. In some embodiments, the fibers are of irregular shapes including, for example, linear, serpentine or curved shapes. In some embodiments, the fiber may have demineralized particles in or on the fiber however some of the original mineral content may be retained when desirable for a particular embodiment. In various embodiments, the fibers may have mineralized portions in or on them. In some embodiments, the fibers have a combination of demineralized and mineralized portions in or on them.

Non-fibrous includes configurations that are triangular, square, cube shapes, or powder form.

The terms "three-dimensional printing system," "three-dimensional printer," "printing," describe various solid free-form manufacturing techniques for making three-dimensional articles or objects by selective deposition, jetting, fused deposition modeling, multijet modeling, and other additive manufacturing techniques now known in the art or that may be known in the future that use a build material or ink to fabricate three-dimensional objects.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The present disclosure provides implantable compositions and methods that are in fiber form that, in some embodiments, allow osteogenesis, osteoinduction and/or osteoconduction. These fibers can be manufactured to bind together and form an implant that can be used to treat, among other things, a bone defect.

Fibers

The fibers of the present application can be made to enhance mechanical entanglement with one another and be used, for example, as a bone void filler. In some embodiments, the bone void filler comprises bone materials such as autograft, allograft, or xenograft. Turning now to FIGS. 1-29, provided is a fiber of an implantable composition. In some embodiments, the fiber 20 comprises a binding surface 12 and a non-binding surface 14 along longitudinal axis LA. The binding surface of the fiber is specifically designed to bind or entangle with another fiber. The binding surface 12 of the fiber is shown in FIG. 1 as a hooked portion, which can bind another binding surface of a second set of fibers. The fiber of FIG. 1 has a non-binding surface 14, which, in this embodiment is linear. A binding surface includes a surface on a portion of a fiber that is designed to mechanically bind or entangle with another fiber.

A non-binding surface includes a surface on a portion of a fiber that is designed not to mechanically bind or entangle with another fiber if it contacts another non-binding surface. For example, if a linear surface contacts another fiber that has a linear surface, the two fibers will not mechanically entangle. However, if a non-binding surface of one fiber contacts a binding surface of another fiber, for example, a liner portion of one fiber contacts a hooked portion of another fiber, there will be binding or mechanical entanglement.

In some embodiments, the entanglement among fibers are enhanced by the flexibility of the fibers, for example, when fibers are wrapping. In some embodiments, the surface roughness of the fiber itself, and/or the porosity of the fibers (for example, by adding a porogen to the fibers or altering polymer curing) can also enhance interfaces between fibers making them have enhanced entanglement.

Figure 2:
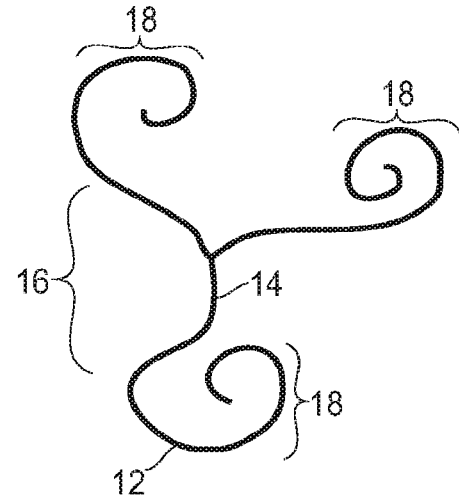
FIG. 2 illustrates an embodiment of a top view of an exemplary fiber having a body portion near the non-binding surface and end portions near the binding surfaces.

FIG. 2 illustrates an embodiment of a top view of an exemplary fiber having a body portion 16 near the non-binding surface 14 and end portions 18 near the binding surface 12, which are in hook configurations that allow binding or mechanical entanglement with other fibers. Shown are three binding surfaces.

Figure 3:
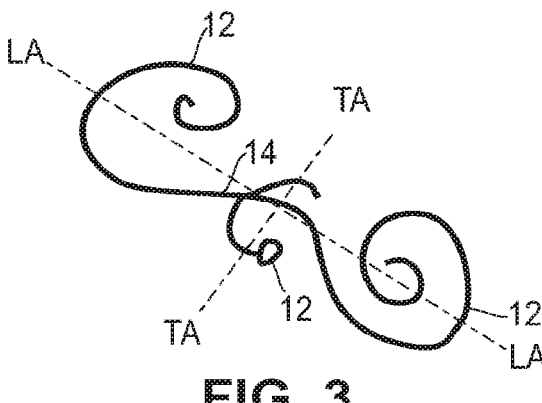
FIG. 3 illustrates an embodiment of a top view of an exemplary fiber having a binding surface and a non-binding surface.

FIG. 3 illustrates an embodiment of a top view of an exemplary fiber having a binding surface 12 and a non-binding surface 14 and another binding surface 13 along the transverse axis (TA) that enhances binding or mechanical entanglement with other fibers. The binding surface 13 is shown as a hook and loop.

Figure 4:
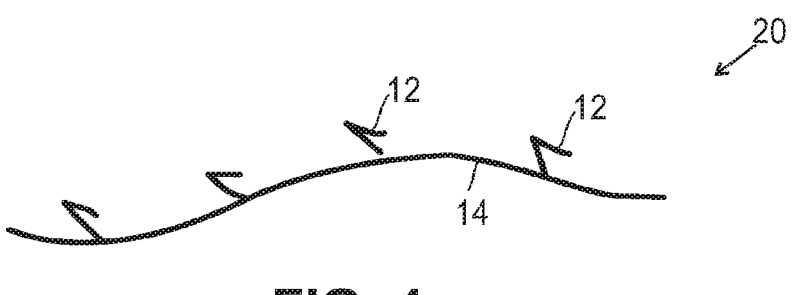
FIG. 4 illustrates an embodiment of a top view of an exemplary fiber having a binding surface and a non-binding surface.

FIG. 4 illustrates an embodiment of a top view of an exemplary fiber having a binding surface 12 and a non-binding surface 14. In this embodiment, there is a plurality of binding surfaces shown as barbs or angular projections that are disposed on one side of the fiber.

Figure 5:
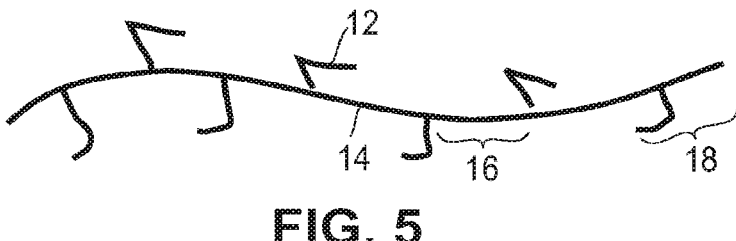
FIG. 5 illustrates an embodiment of a top view of an exemplary fiber having a binding surface and a non-binding surface.

FIG. 5 illustrates an embodiment of a top view of an exemplary fiber having a binding surface 12 and a non-binding surface 14. In this embodiment, there is a plurality of binding surfaces shown as barbs or angular projections that are disposed on both sides of the fiber.

Figure 6:
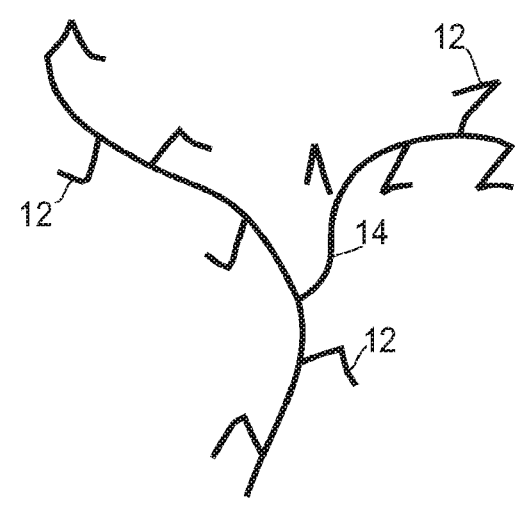
FIG. 6 illustrates an embodiment of a top view of an exemplary fiber having a binding surface and a non-binding surface.

FIG. 6 illustrates an embodiment of a top view of an exemplary fiber having a binding surface 12 and a non-binding surface 14. In this embodiment, there is a plurality of binding surfaces shown as barbs or angular projections that are branched about the fiber.

Figure 7:
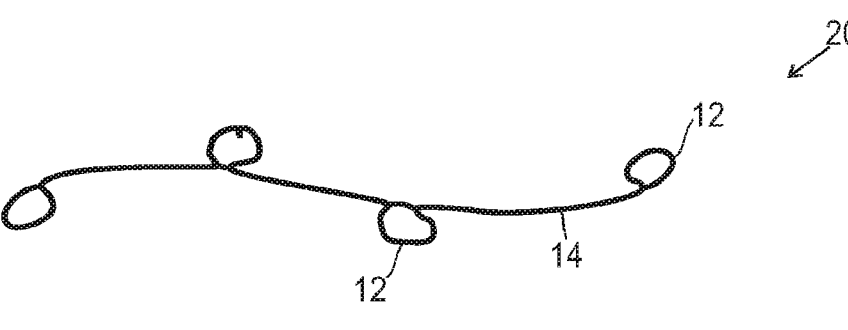
FIG. 7 illustrates an embodiment of a top view of an exemplary fiber having a binding surface and a non-binding surface.

FIG. 7 illustrates an embodiment of a top view of an exemplary fiber having a binding surface 12 and a non-binding surface 14. In this embodiment, there is a plurality of binding surfaces shown as loops that are on alternating sides of the longitudinal axis of the fiber.

Figure 8:
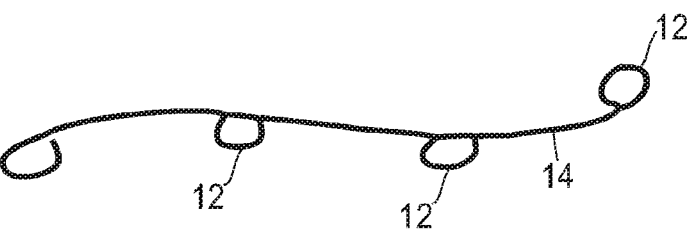
FIG. 8 illustrates an embodiment of a top view of an exemplary fiber having a binding surface and a non-binding surface.

FIG. 8 illustrates an embodiment of a top view of an exemplary fiber having a binding surface 12 and a non-binding surface 14. In this embodiment, there is a plurality of binding surfaces shown as loops that are on alternating sides of the longitudinal axis of the fiber in a unique pattern of three on one side and one on the other side. It will be understood by those of ordinary skill in the art that the fiber can be designed to have many patterns and alternating binding surfaces.

Figure 9:
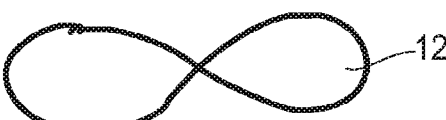
FIG. 9 illustrates an embodiment of a top view of an exemplary fiber having a binding surface.

FIG. 9 illustrates an embodiment of a top view of an exemplary fiber having a binding surface 12 shown as two loops that unite.

Figure 10:
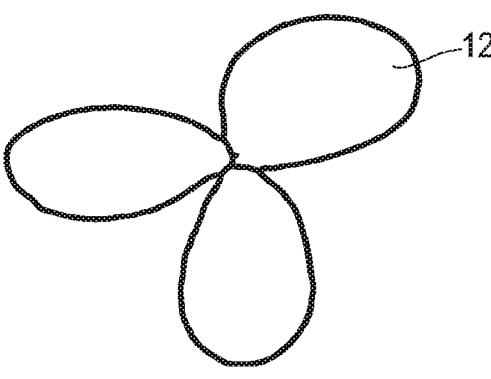
FIG. 10 illustrates an embodiment of a top view of an exemplary fiber having a binding surface.

FIG. 10 illustrates an embodiment of a top view of an exemplary fiber having a binding surface 12 shown as three loops that unite.

Figures 11, 12:
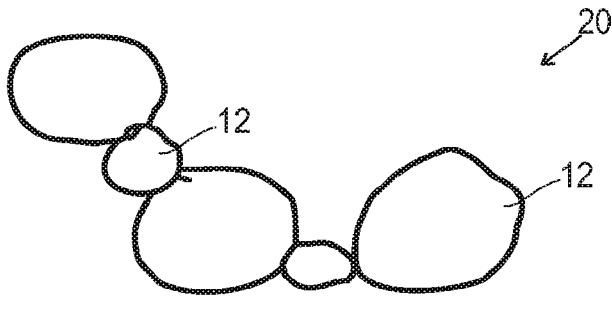
FIG. 11 illustrates an embodiment of a top view of an exemplary fiber having a binding surface.
FIG. 12 illustrates an embodiment of a top view of an exemplary fiber having a binding surface and a non-binding surface.

FIG. 11 illustrates an embodiment of a top view of an exemplary fiber having a binding surface 12. In this embodiment, there is a plurality of binding surfaces shown as a chain of loops that are alternating diameter patterns, larger diameters and smaller diameters. The loops can mechanically entangle with another loop on the same or different fiber.

FIG. 12 illustrates an embodiment of a top view of an exemplary fiber having a binding surface 12 and a non-binding surface 14. In this embodiment, there is a plurality of binding surfaces shown as a chain of loops that are spaced apart by non-binding surfaces, which are relatively straight.

FIG. 13 illustrates an embodiment of a top view of an exemplary fiber having a binding surface 12 and a non-binding surface 14. In this embodiment, there is a plurality of binding surfaces as the fiber is in a curled configuration.

FIG. 14 illustrates an embodiment of a top view of an exemplary fiber having a binding surface 12 and a non-binding surface 14. In this embodiment, there is a plurality of binding surfaces as the fiber is in a curled configuration and the curls or loops that are the binding surfaces alternate in size on one side of the fiber.

FIG. 15 illustrates an embodiment of a top view of an exemplary fiber having a binding surface 12 and a non-binding surface 14. In this embodiment, there is a plurality of binding surfaces as the fiber is in a curled configuration and the curls or loops that are the binding surfaces alternate in size on one side of the fiber.

FIG. 16 illustrates an embodiment of a top view of an exemplary fiber having a binding surface 12 and a non-binding surface 14. In this embodiment, there is a plurality of binding surfaces as the fiber is in a 3-dimensional helical configuration in x, y and z planes or spiral configuration and the curves that are the binding surfaces alternate in size on one side of the fiber. It will also be understood that, in some embodiments, the fiber can be in a flat conformation.

FIG. 17 illustrates an embodiment of a top view of an exemplary fiber having a binding surface 12 and a non-binding surface 14. In this embodiment, there is a plurality of binding surfaces as the fiber is in a long helical or spiral configuration and the curves that are the binding surfaces are on one side of the fiber.

Figure 18:
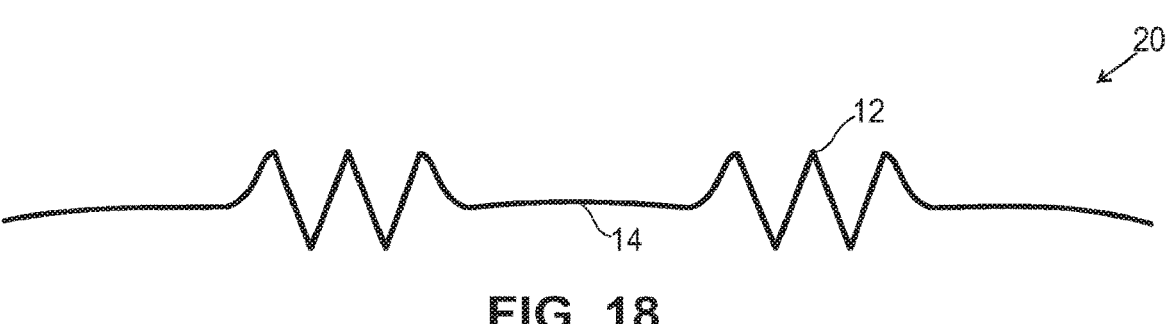
FIG. 18 illustrates an embodiment of a top view of an exemplary fiber having a binding surface and a non-binding surface.

FIG. 18 illustrates an embodiment of a top view of an exemplary fiber having a binding surface 12 and a non-binding surface 14. In this embodiment, there is a plurality of binding surfaces as the fiber has angular or zig zag portions. These angular or zig zag portions allow the fiber to extend or have elastic characteristics, which help binding or mechanically entangling with other fibers. The non-binding surfaces can be a relatively linear portion disposed between the angular or zig zag portions that are the binding portions.

Figure 19:
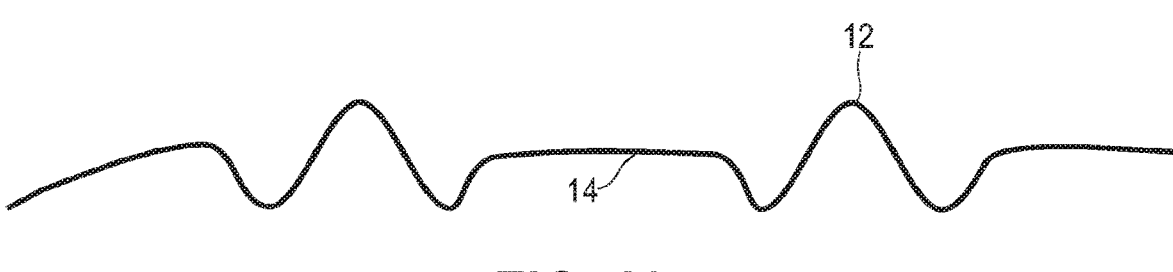
FIG. 19 illustrates an embodiment of a top view of an exemplary fiber having a binding surface and a non-binding surface

FIG. 19 illustrates an embodiment of a top view of an exemplary fiber having a binding surface 12 and a non-binding surface 14. In this embodiment, there is a plurality of binding surfaces as the fiber has sinusoidal portions, where the peaks and trough of the wave are the binding portions.

Figure 20:
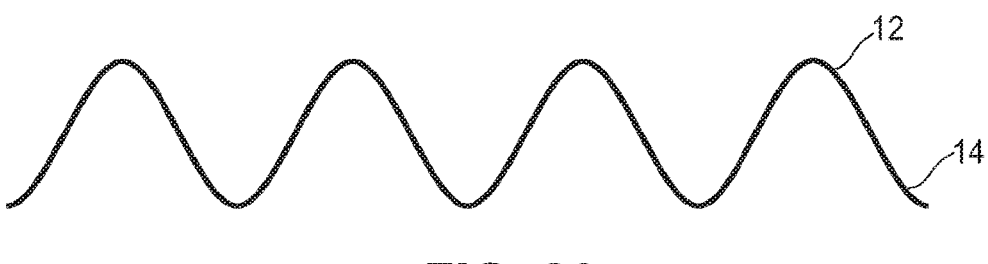
FIG. 20 illustrates an embodiment of a top view of an exemplary fiber having a binding surface and a non-binding surface.

FIG. 20 illustrates an embodiment of a top view of an exemplary fiber having a binding surface 12 and a non-binding surface 14. In this embodiment, there is a plurality of binding surfaces as the fiber has continuous sinusoidal portions, where the peaks and trough of the wave are the binding portions. The non-binding surfaces can be a relatively linear portion disposed between the peaks and troughs.

Figure 21:
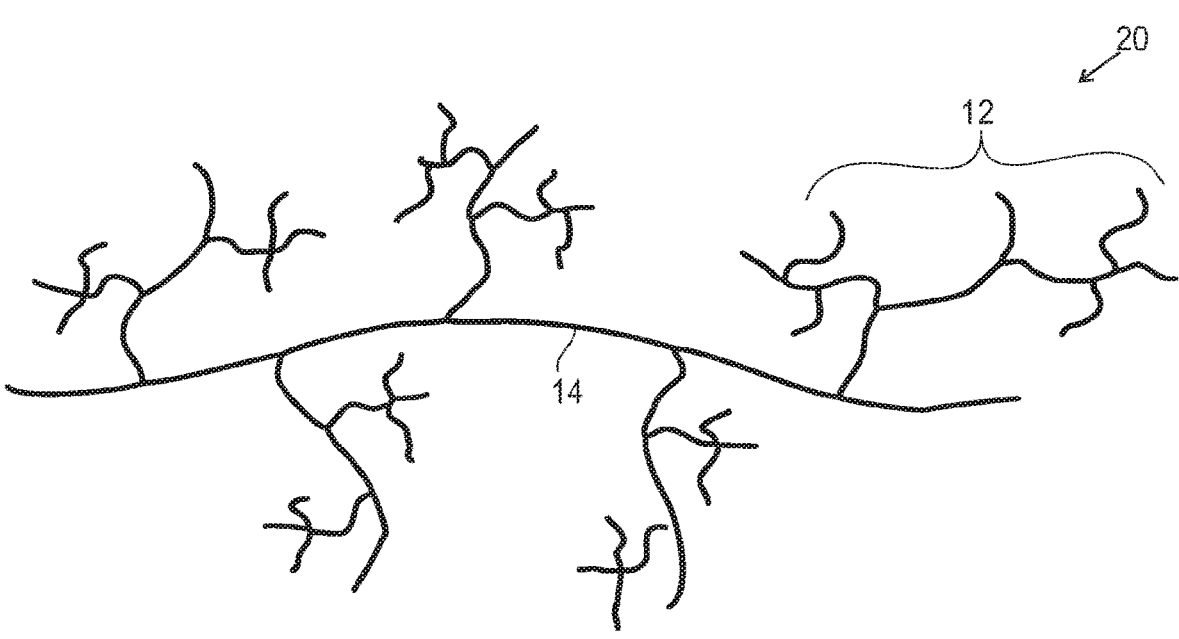
FIG. 21 illustrates an embodiment of a top view of an exemplary fiber having a binding surface and a non-binding surface.

FIG. 21 illustrates an embodiment of a top view of an exemplary fiber having a binding surface 12 and a non-binding surface 14. In this embodiment, there is a plurality of binding surfaces shown as branched portions of the fiber that alternate on different sides of the fiber, which help binding or mechanically entangling with the same fiber or other fibers. The non-binding surfaces can be a relatively linear portion disposed between the branched portions.

Figure 22:
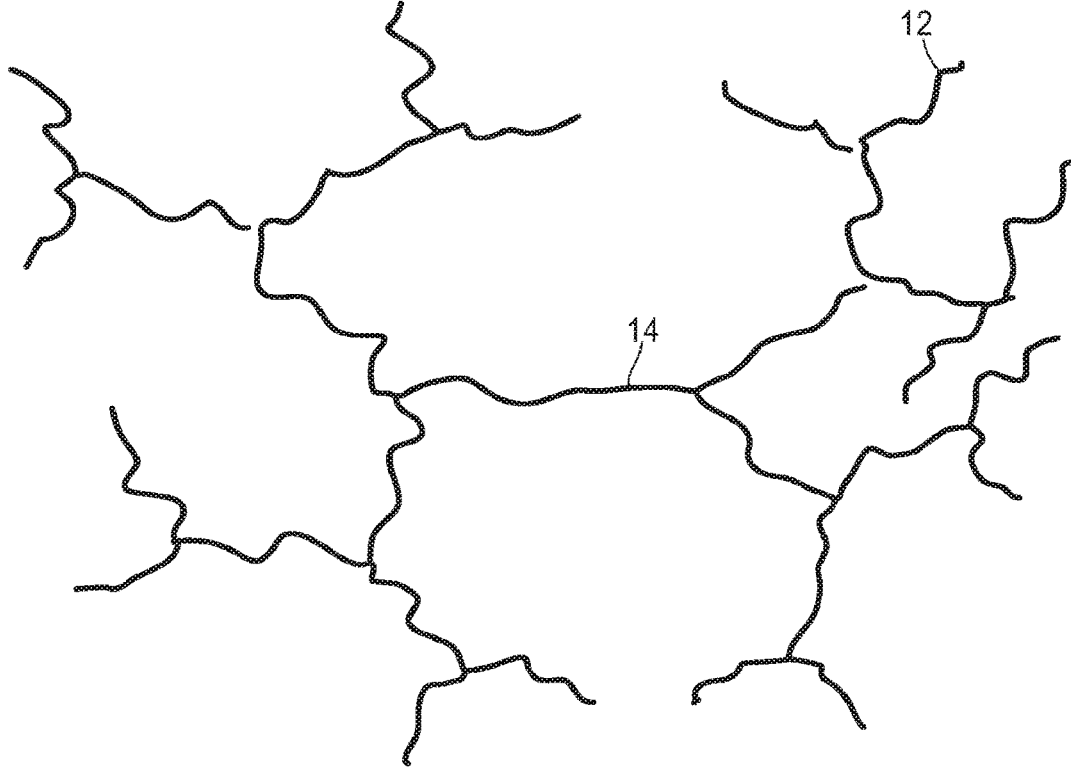
FIG. 22 illustrates an embodiment of a top view of an exemplary fiber having a binding surface and a non-binding surface.

FIG. 22 illustrates an embodiment of a top view of an exemplary fiber having a binding surface 12 and a non-binding surface 14. In this embodiment, there is a plurality of binding surfaces shown as branched portions of the fiber that on different sides of the fiber, which help binding or mechanically entangling with the same fiber or other fibers. The non-binding surfaces can be a relatively linear portion disposed in the center of the branched portions.

Figure 23:
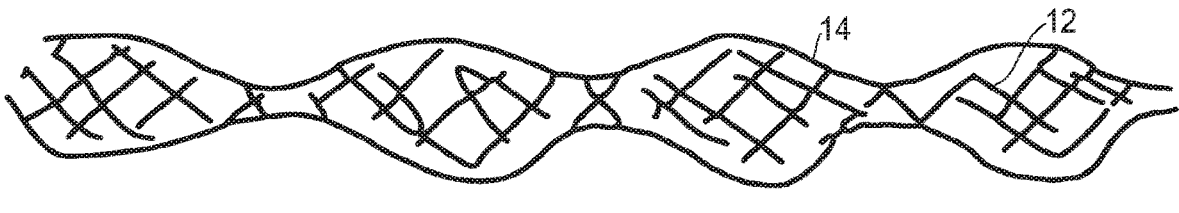
FIG. 23 illustrates an embodiment of a top view of an exemplary fiber having a binding surface and a non-binding surface.

FIG. 23 illustrates an embodiment of a top view of an exemplary fiber having a binding surface 12 and a non-binding surface 14. In this embodiment, there is a plurality of binding surfaces shown as ribbon portions of the fiber, which help binding or mechanically entangling with the same fiber or other fibers.

Figure 24:
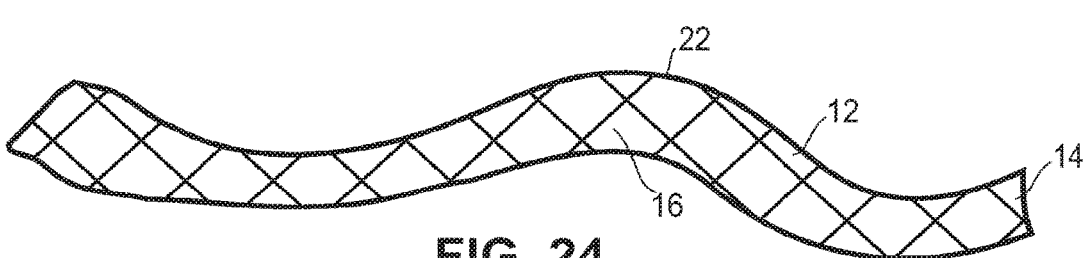
FIG. 24 illustrates an embodiment of a top view of an exemplary fiber having an edge and a body portion.

FIG. 24 illustrates an embodiment of a top view of an exemplary fiber having an edge 22 and a body portion 16. In this embodiment, there is a plurality of binding surfaces 12 shown as sheet portions of the fiber, which help binding or mechanically entangling with the same fiber or other fibers. The non-binding surface 14 is generally linear.

Figure 25:
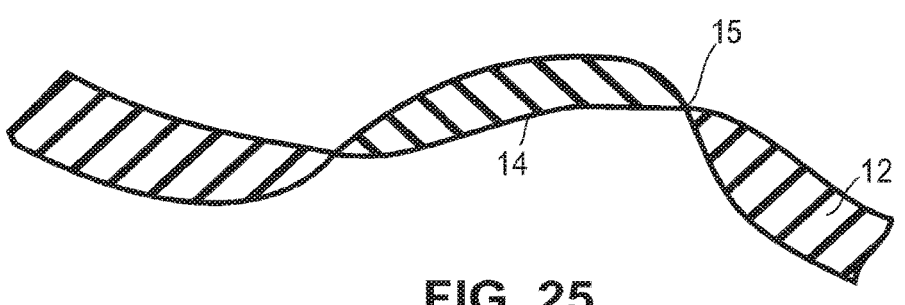
FIG. 25 illustrates an embodiment of a perspective view of a fiber having a binding surface and a non-binding surface.

FIG. 25 illustrates an embodiment of a perspective view of a fiber having a binding surface 12 and a non-binding surface 14. In this embodiment, there is a plurality of binding surfaces 12 shown as sheet portions of the fiber that have twist portions 15, which help binding or mechanically entangling with the same fiber or other fibers. The non-binding surface 14 is generally linear.

Figure 26:
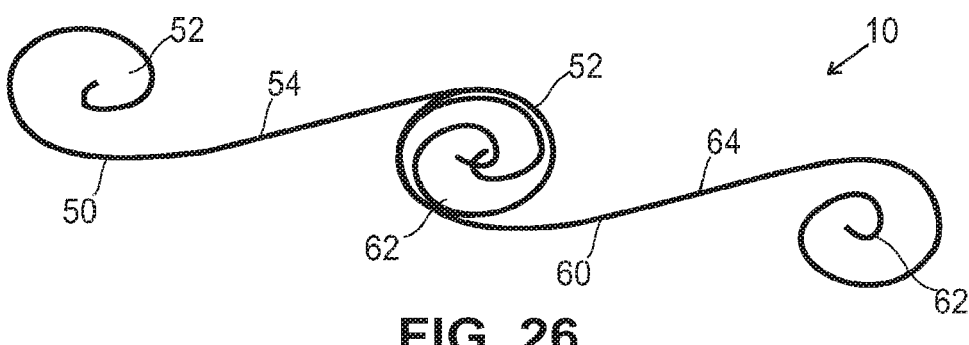
FIG. 26 illustrates an embodiment of an implantable composition comprising a first set of fibers and a second set of fibers, the first set of fibers comprising a first binding surface, the second set of fibers comprising a second binding surface, the first binding surface of the first set of fibers configured to bind at least at or near the second binding surface of the second set of fibers and the second set of fibers configured to bind at least at or near the first binding surface of the first set of fibers. The fibers are mechanically entangled together.

FIG. 26 illustrates an embodiment of an implantable composition 10 comprising a first set of fibers 50 and a second set of fibers 60, the first set of fibers comprising a first binding surface 52, the second set of fibers comprising a second binding surface 62, the first binding surface of the first set of fibers configured to bind at least at or near the second binding surface of the second set of fibers and the second set of fibers configured to bind at least at or near the first binding surface of the first set of fibers. The fibers are mechanically entangled together. The non-binding surface 54 of the first set of fibers is generally linear and is not bound to the second set of fibers. The non-binding surface 64 of the second set of fibers is generally linear and is not bound to the first set of fibers. It will be understood that a set can be one or more fibers.

Figure 27:
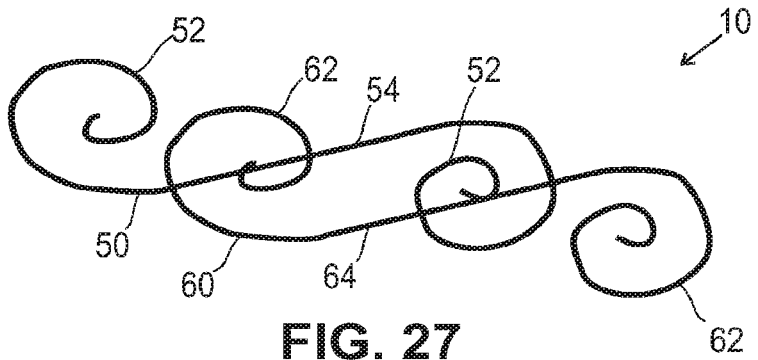
FIG. 27 illustrates an embodiment of an implantable composition comprising a first set of fibers and a second set of fibers, the first set of fibers comprising a first binding surface, the second set of fibers comprising a second binding surface, the first binding surface of the first set of fibers configured to bind at least at or near the second binding surface of the second set of fibers and the second set of fibers configured to bind at least at or near the first binding surface of the first set of fibers. The fibers are mechanically entangled together.

FIG. 27 illustrates an embodiment of an implantable composition 10 comprising a first set of fibers 50 and a second set of fibers 60, the first set of fibers comprising a first binding surface 52, the second set of fibers comprising a second binding surface 62, the first binding surface of the first set of fibers configured to bind at least at or near the second binding surface of the second set of fibers and the second set of fibers configured to bind at least at or near the first binding surface of the first set of fibers. The fibers are mechanically entangled together. The non-binding surface 54 of the first set of fibers is generally linear and is not bound to the second set of fibers. The non-binding surface 64 of the second set of fibers is generally linear and is not bound to the first set of fibers. In some embodiment, the entanglement between the binding surface and the non-binding surface is less robust than the entanglement between the binding surface and the binding surface.

Figure 28:
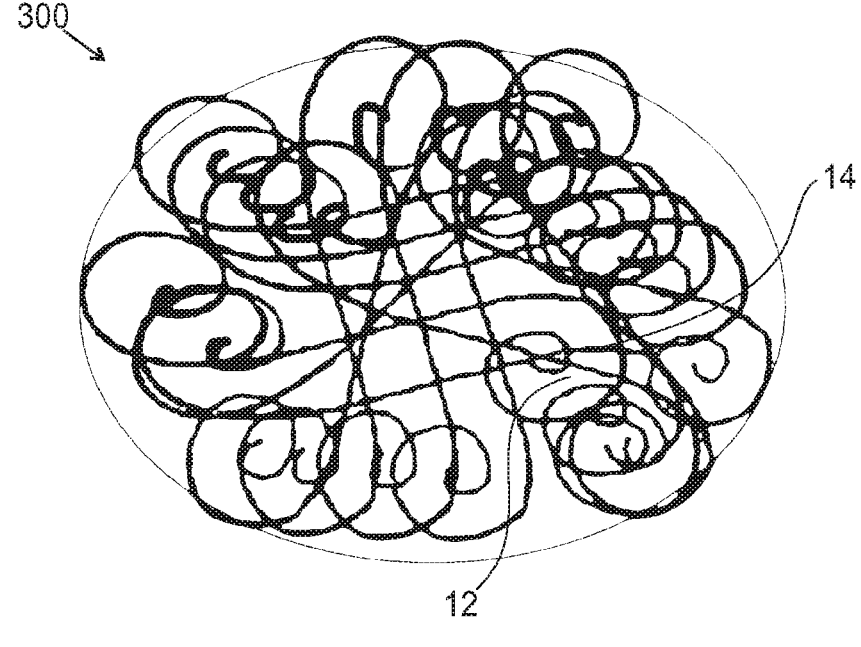
FIG. 28 illustrates an embodiment of a plurality of entangled fibers in an implantable composition that form a coherent mass that can be molded, lyophilized, hydrated, and/or shaped before implanting at the target tissue site.

FIG. 28 illustrates an embodiment of a plurality of entangled fibers in an implantable composition that form a coherent mass 300 that can be mixed, and/or molded, and/or lyophilized, and/or hydrated, and/or shaped before implanting at the target tissue site. Each fiber in the coherent mass comprises a binding surface 12 and a non-binding surface 14. The coherent mass has the fibers that have hook portions and the fibers are ordered as opposed to a random conformation. The fibers are also the same type of fibers having hooks as shown in FIG. 1.

Figure 29:
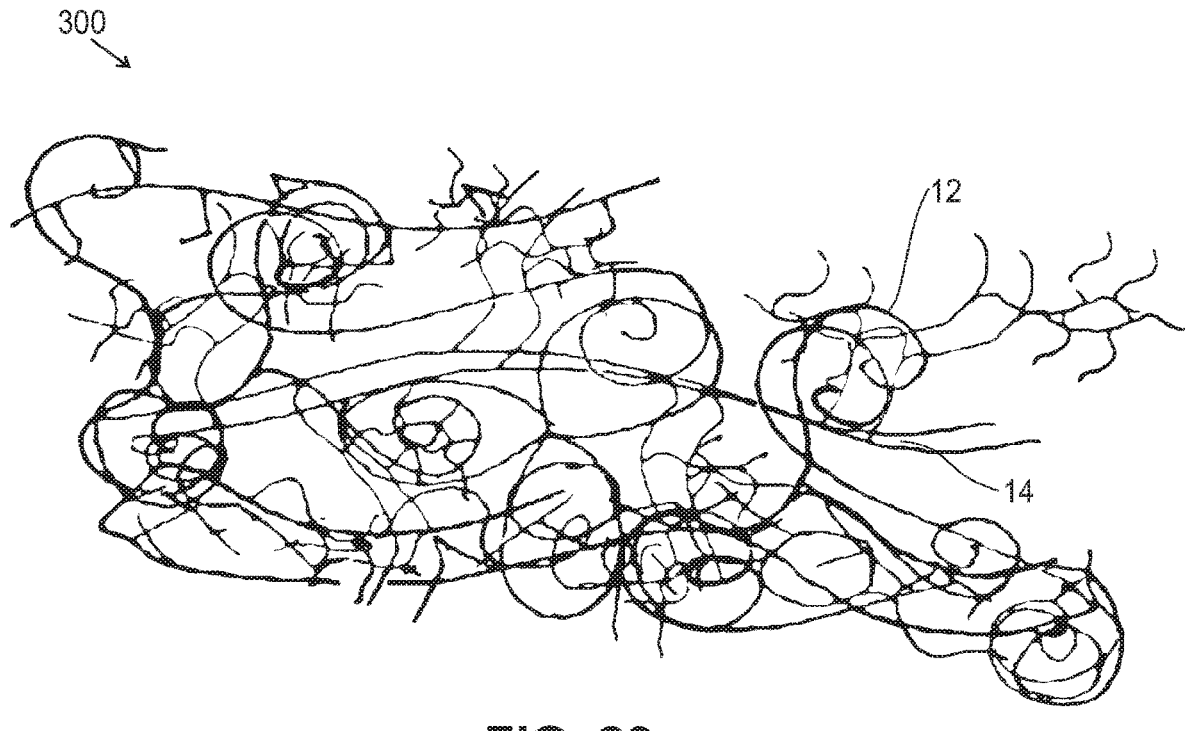
FIG. 29 illustrates an embodiment of a plurality of entangled fibers in an implantable composition that form a coherent mass that can be molded, lyophilized, hydrated, and/or shaped before implanting at the target tissue site.

FIG. 29 illustrates an embodiment of a plurality of entangled fibers in an implantable composition that form a coherent mass 300 that can be mixed, and/or molded, and/or lyophilized, and/or hydrated, and/or shaped before implanting at the target tissue site. Each fiber in the coherent mass comprises a binding surface 12 and a non-binding surface 14. The coherent mass has the fibers that have hook portions as in FIG. 1 and branched portions in FIG. 21 in combination with each other. The coherent mass of fibers is in a random conformation as opposed to an ordered conformation.

The fibers of the implantable composition, in some embodiments, comprise both 3D printed fibers and DBM fibers. In some embodiments, 3D printed fibers, after being printed, can be combined with DBM fibers to create 3D printed/milled bone fibers combinations. The combination of these two fibers can be completed prior to or after they are made into a coherent mass.

The fibers of the implantable composition, in some embodiments, do not require binding agents between two sets of fibers. In some embodiments, the binding can be achieved through mechanically entanglement. In some embodiments, the mechanical entanglement can be accomplished by agitating, stirring, mixing or shaking or other physical movement of the fibers.

In some embodiments, the implantable composition requires an additional binding agent. Examples of suitable binding agents or carrier that optionally can be included after the coherent mass is formed include, but are not limited to glycerol, polyglycerol, polyhydroxy compound, for example, such classes of compounds as the acyclic polyhydric alcohols, non-reducing sugars, sugar alcohols, sugar acids, monosaccarides, disaccharides, water-soluble or water dispersible oligosaccarides, polysaccarides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; glycosaminoglycans, for example, hyaluronic acid; polyoxyethylene-polyoxypropylene copolymer, for example, of the type known and commercially available under the trade names Pluronic and Emkalyx, polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

In some embodiments, the first set of fibers and the second set of fibers comprise a resorbable polymer, a non-resorbable polymer, an ink of organic material, an ink of synthetic material, a therapeutic agent, a soft tissue, a bone material or a combination thereof. In some embodiments, the first set of fibers and the second set of fibers comprise bone material disposed in or on the fibers. In some embodiments, the first set of fibers and the second set of fibers are configured to be molded into a putty, paste or are configured to be lyophilized. In some embodiments, the first set of fibers and the second set of fibers are made by additive manufacturing, subtractive manufacturing, stereolithography, extrusion molding, ultraviolet light printing or a combination thereof. In some embodiments, the ratio of the binding surface to non-binding surface is about 5:1, about 4:1, about 3:1, about 2:1, about 1:1, about 1:5, about 1:4, about 1:3, or about 1:2. In accordance with some embodiments, the printing material for use by the 3-D printer with, in or on a bone or ceramic material may be supplemented, further treated, or chemically modified with one or more bioactive agents, fibrous bone grafts or patient autograft.

The fiber may be configured to allow ingrowth of cells while also retaining the osteogenic material within. In some embodiments, the print head is configured to extrude the fiber having a predetermined thickness. In some embodiments, the fiber has about 1 cm or less in diameter, about 4 cm or less in length, about 1 mm or less in thickness. In some embodiments, the fiber is about 0.01 mm or less in diameter, about 0.01 mm or less in length, and/or about 0.01 mm or less in thickness.

In some embodiments, the fibers have a thickness or a diameter of about 0.01 mm to about 2.0 mm. In some embodiments, fibers have a thickness of about 0.05 mm to about 1.0 mm, or about 0.1 to about 0.5 mm. The thickness of fibers may be uniform along the length of each fiber, or varied across the length of each fiber. In some embodiments, some fibers have a greater thickness than other fibers in the coherent mass. Fibers may be sized to allow for customizable pore sizes between fibers. In some embodiments, a porous fiber is configured to facilitate transfer of substances and/or materials surrounding the surgical site. Upon implantation to a surgical site, the implantable composition may participate in, control, or otherwise adjust, or may allow penetration of the implantable composition by surrounding materials, such as cells or tissue. In some embodiments, the fiber has various cross-sectional shapes such as, for example, rectangular, oval, polygonal, irregular, undulating, or lobed.

In various embodiments, the fibers may be sized according to the needs of a particular application. For example, the fiber may include dimensions between about 1 mm to about 100 mm in diameter. In some embodiments, the fiber includes a diameter of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, the fiber includes a length or depth from about 0.1 cm to about 10 cm. In some embodiments, the fiber includes a length or depth of about 1 cm, 2 cm, 3 cm, 4 cm, 5 cm, 6 cm, 7 cm, 8 cm, 9 cm, or 10 cm. The desired dimensions can be selected by the user and the computer system can print the implant according to the selection.

In various embodiments, based on the foregoing dimensions, the volume of a 3-D printed fiber can be easily calculated. For example, in some embodiments, a 3-D printed fiber having a diameter of 0.5 cm and a length of 0.1 cm would provide a volume of 0.02 cc. In other embodiments, a 3-D printed fiber having a diameter of 1 cm and a length of 1 cm would provide a volume of 0.79 cc. In yet other embodiments, a 3-D printed fiber having a diameter of 1.5 cm and length of 3 cm would provide a volume of 5.3 cc.

In some embodiments, the fibers are extruded onto the printing surface in a wave-like configuration having alternating peaks and troughs. In some embodiments, the printing surface is moving in alternating clockwise and counter-clockwise directions while material is extruded onto the surface to create sinusoidal shaped waves having evenly shaped curves on the peaks and crests. In some embodiments, the peaks and crests of the waves are pointed to impart variable characteristics to fibers. In some embodiments, the fibers are extruded adjacent to one another such that the peak of a first fiber is extruded to contact the crest of an adjacent second fiber. In some embodiments, the coherent mass may be created entirely from fibers having this configuration. Wave-shaped fibers impart flexibility and stretchable characteristics onto the manufactured fiber. The wavelength of the wave-shaped fibers may be altered to customize stretchability of the fiber. For example, fibers having shorter wavelengths will be able to be stretched more than fibers having longer wavelengths. In some embodiments, the stretchability of the fiber is uniform across its length. In some embodiments, the fiber includes regions of increased stretchability according to the needs of a surgical application. In some embodiments, the non-binding surface can incorporate wave like features to enhance stretchability of the fibers.

The shape, size, thickness, and other structural characteristics, of the fiber for example, architecture, may be customized for the desired application. For example, to optimize cell or fluid migration through the fiber, the pore size may be optimized for the viscosity and surface tension of the fluid or the size of the cells. For example, pore sizes between fibers on the order of approximately 100-200 μm may be used if cells are to migrate through the fiber. In some embodiments, cells are to migrate through the entangled matrix of fibers. In other embodiments, the wave-shaped fibers may be extruded to have larger peaks and crests and the size of the pores may be larger. For example, in some embodiments, the pore size between fibers may be about 0.1 mm to about 5 mm, about 0.5 mm to about 3 mm, or about 1 mm to about 2 mm. In some embodiments, the pore size within the fiber may be about 0.1 mm to about 5 mm, about 0.5 mm to about 3 mm, or about 1 mm to about 2 mm. The size may be controlled by printing the fibers and by controlling the thickness of fibers extruded and/or sintered on the printing surface.

Printing Devices

Provided are 3-D printing devices and methods of use for creating, in some embodiments, a fiber of the implantable composition. Also provided are 3-D printing devices including a moving printing surface to create such fiber in a continuous process or in some embodiments, in a batch process. In some embodiments, the moving print surface is configured to facilitate continuous or near-continuous mass production of fibers. Further provided are devices and methods for 3-D printing onto a moving printing surface by continuous extrusion instead of stratified layers. Additionally, provided are devices and methods for creating structures having a filamentous design that can entangle and are strong, flexible, stretchable and biocompatible.

In FIGS. 35-38, a fiber is being printed as a result of instructions received from the computer. In some embodiments, a fiber as discussed in FIGS. 1-25 is formed from material extruded from a print head 502 of a 3-D printing device 500. The fiber is extruded directly onto printing surface 508. The binding surface may be extruded in various patterns, and may be sized according to the requirements of a particular application. For example, the binding surface may be extruded from the print head in a weave pattern in which the binding surfaces are interwoven with one another such that they form another binding surface, for example as shown in FIGS. 23-25. In other embodiments, the binding surface may be extruded in other ways. For example, horizontal rows of the binding surface may be extruded in a first step, and in second step vertical rows of the binding surface may be extruded on top of the horizontal rows. The printing material for the fiber may include bone material (e.g., DBM particles, allograft tissue particles, cortical bone particles, ceramic particles, etc.) uniformly disposed throughout the fiber. The material to make fiber (e.g., biodegradable polymer) and the bone material may be combined into one print ink and print head, or it can be in separate print inks or print heads 502, 504 and then printed together or separately until the desired fiber is formed. A radiation source 506, such as laser may be configured to sinter the extruded rows together to form the fiber.

In some embodiments, the dimensions of printing surface allows for printing a fiber of different dimensions, shapes, binding and non-binding surfaces that correspond to printing surface (for example, circular, rectangular, square, etc.) The movement of printing surface shown as M in FIG. 36, allows the implantable composition (for example, fiber 20 in FIG. 4) to be printed continuously so that there is a reduced need for reactivating the machine and reduced waste of raw materials. The computer system can calculate the proper volume, length, width, and thickness of the fiber to match the volume, length, width, and thickness of the bone defect site or make single fibers of various configurations to be mechanically entangled.

In some embodiments, a computer implemented method for producing an implantable composition is provided. The method comprises generating a 3-D digital model of the implantable composition, the 3-D digital model being of a first set of fibers and a second set of fibers, the first set of fibers comprising a first binding surface and a first non-binding surface, the second set of fibers comprising a second binding surface and a second non-binding surface, the first binding surface of the first set of fibers configured to bind at least at or near the second binding surface of the second set of fibers and the second set of fibers configured to bind at least at or near the first binding surface of the first set of fibers; and storing the 3-D digital model on a database coupled to a processor, the processor having instructions for selecting the implant material based on the stored 3-D digital model and for instructing a print surface of a 3-D printer to print the implantable composition on the print surface.

In some embodiments, the first binding surface of the first set of fibers comprises a curl portion, a hook portion, a branched portion, a barbed portion, a looped portion, a chain portion, a helical portion, a spiral portion, an angular portion, a twist portion, a ribbon portion, a sinusoidal portion, or a zigzag portion and the second binding surface of the second set of fibers also comprises a curl portion, a hook portion, a branched portion, a barbed portion, a looped portion, a chain portion, a helical portion, a spiral portion, an angular portion, a twist portion, a ribbon portion, a sinusoidal portion, or a zigzag portion.

In some embodiments, the fiber comprises a body portion that is solid like a ribbon, and/or porous like a porous ribbon. In some embodiments, the body portion comprises filament bridges like a ladder between the edges.

In some embodiments, the first non-binding surface of the first set of fibers comprises a straight portion and the second non-binding surface of the second set of fibers also comprises a straight portion and the implantable composition is a bone void filler.

In some embodiments, the first set of fibers and the second set of fibers comprise a resorbable polymer, a non-resorbable polymer, an ink of organic material, an ink of synthetic material, a therapeutic agent, a soft tissue, a bone material or a combination thereof.

In some embodiments, the first set of fibers and the second set of fibers comprise bone material disposed in or on the fibers.

In some embodiments, the first set of fibers and the second set of fibers are configured to be molded into a putty, paste or are configured to be lyophilized.

In some embodiments, before the 3-D digital model of the implantable composition is generated, a 3-D digital model of an intended tissue repair site is generated, and the 3-D digital model of the implantable composition is generated to fit within the 3-D digital model of the tissue repair site.

In some embodiments, before the 3-D digital model of the implantable composition is generated, a type of material that the 3-D digital model of the implantable composition is made from is selected.

Turning now to FIGS. 35-38, provided is a 3-D printing device 500 for making the implantable composition, such as a fiber, 3-D printing is typically done in 2 dimensions, one layer at a time. Material is laid out on a flat surface and the three dimensional structures are built up one layer at a time, usually through a melting or sintering process, in some embodiments, a 3-D printer having a moving printing surface is provided to allow printing the fibers in a continuous process. In some embodiments, a print head applies material to the print surface through continuous extrusion instead of stratified layers, as is done by traditional 3-D printing devices. In some embodiments, the 3-D printing device creates stronger structures and generates less waste than traditional 3-D printing devices.

As shown in FIGS. 35-38, provided is a 3-D printing device for use in making the implantable composition. The 3-D printing device includes a conveyor belt 510 having a base 512 and a printing surface 508 configured for planar movement. In some embodiments, the base is movable in the x-y plane and is laterally movable in both the x axis and the y axis for precise positioning of the printing surface. The printing surface, in some embodiments, is fixedly disposed with a table 514 such that lateral movement of the base causes lateral movement of the printing surface. Movement of the base allows for positioning of the printing surface relative to the print head to facilitate depositing materials onto the printing surface, as discussed herein. The implantable composition may include fibers having bone material (e.g., DBM particles, allograft tissue particles, cortical bone particles, etc.) uniformly disposed throughout the fiber.

In some embodiments, the printing surface includes other cross-sectional shapes, such as, for example, rectangular, oval, polygonal, irregular, undulating, or lobed. For example, the printing surface may have a rectangular cross-section extending along a longitudinal axis. The surface can tip or veer along a longitudinal axis of the printing surface. This allows printing of a square or rectangular implant (e.g., fiber), as the print surface moves, the implant will take the shape of the print surface. The shape of printing surface may define the shape of the fiber created, as shown in FIGS. 1-25. The implantable composition (e.g., fiber) may include bone material (e.g., DBM particles, allograft tissue particles, cortical bone particles, etc.) uniformly disposed throughout the implantable composition. In some embodiments, for example, the printing surface can rotate along a rotational axis 360 degrees clockwise and/or counterclockwise to print the implant. In some embodiments, the printing surface is not continuous, and the printed fibers maybe extracted from the printing surface before the next batch of fibers is printed.

In some embodiments, the 3-D printing device further includes the print head, such as, for example, an applicator that is movable in a direction transverse to the plane of movement for the base. In some embodiments, a print head is movable in the z axis, to allow for different size fibers, variable surface structures and to control the thickness of the extruded layer. Thus, the print head is movable to have an adjustable distance from the printing surface. Additionally, the print head is movable to accommodate printing surfaces having various diameters or printing surfaces having gradient diameters. In some embodiments, the print head is also movable in the x and y planes parallel with the plane of movement for the base. Thus, in some embodiments, the print head is movable in an opposite direction from the movement of the printing surface to facilitate faster printing.

In some embodiments, the printing surface is treated with an adhesive material. The adhesive material may be textured or coated onto the printing surface. The adhesive may be heat sensitive or heat activated such that the printing surface becomes adhesive to materials of the implantable composition when the printing surface is heated, as discussed herein. An adhesive coating aids in preventing printed material from falling off the printing surface during rotation. In some embodiments, the adhesive is deactivated through cooling.

In some embodiments, the adhesive may be removed by placing the printing surface in a solvent to dissolve the adhesive material. Once the adhesive material is removed, the printed implantable composition on the printing surface may be removed.

In some embodiments, the print head and the printer surface carry an electrical charge such that a voltage could be measured between the print head and the print surface. In some embodiments, the electrical charge is adjusted to improve control and placement of the printed filament on the print surface, for example, by electrowriting. In some embodiments, Melt Electrowriting (MEW) allows the rapid solidification of an electrified jet and the stacking of fibers in centimeter or millimeter scale, for example, manufacturing 780×780-mm sheets of scaffolds/lattice. In this embodiment, MEW is solvent-free and reduces the economic aspect of using separate components in x, y, and z axes.

As shown in FIGS. 35-38, the print head includes a distal opening 520 through which printing material is deposited on the printing surface. A tube portion 522 of the print head includes a first diameter and extends distally to a head portion 524 having a second diameter. In some embodiments, the second diameter is smaller than the first diameter. In various embodiments, the printing material includes a biodegradable polymer.

In some embodiments, the printing material to make the fiber comprises a bioerodible, a bioabsorbable, and/or a biodegradable biopolymer. Examples of suitable biopolymers include but are not limited to poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAM (sucrose acetate isobutyl rate) or combinations thereof. In various embodiments, printing material comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone, poly(ester)amides or a combination thereof. mPEG may be used in the polymer to impart malleability to the polymer. In some embodiments, these biopolymers may also be coated on the fiber to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the implantable composition. In some embodiments, the range of the coating on the implantable composition ranges from about 5 microns to about 250 microns or from about 5 microns to about 200 microns.

In some embodiments, the print head includes an inner lumen 526 and a central feed shaft 528 as illustrated in FIGS. 34-37. The feed shaft is configured to turn feed threads 530 to feed printing material from the proximal end of the print head through the opening. Printing material is maintained in an external reservoir (not shown) and fed into the lumen. In some embodiments, printing material is driven into the lumen by gravity. In some embodiments, the printing material is driven into the lumen by pressure. In some embodiments, the printing material is drawn into the lumen by turning the feed shaft and the feed threads. In some embodiments, the 3-D printing device includes multiple print heads, each configured to deposit printing material onto the printing surface.

In some embodiments, as illustrated in FIGS. 35-38, the 3-D printing device further includes a temperature control unit 560 such as for example a heating or cooling unit connected to the printing surface. In some embodiments, the temperature control unit includes a heating unit. In other embodiments, the temperature control unit includes a cooling unit. In some embodiments, the temperature control unit is used to heat the printing surface through electric heating elements underneath the surface of the printing surface. Sufficient energy may be supplied through such electric conduits to provide a temperature on the surface of the printing surface to melt and bond printing material applied from the print head. In such an embodiment, conduits are electric heating conduits. In some embodiments, where the printing material comprises a highly viscous material, a heated printing surface allows printing material to flow. In other embodiments, the printing material is heated or cooled in a reservoir 570 to allow the desired flowability or viscosity of the printing material to make the implant (e.g., fiber). It will be understood that the fibers including its binding surface and non-binding surface can be printed individually or a plurality of fibers are printed together to form a coherent mass.

In some embodiments, the temperature control unit comprises a cooling unit. The cooling unit is used to cool the printing surface through refrigerant supply and return lines underneath the printing surface. In such an embodiment, the supply and return lines are the conduits. The conduits supply cooling fluid to the printing surface to cool and solidify hot material extruded onto the surface. In alternative embodiments, the reservoir can have the cooling and heating unit to allow cooling or heating of the printing material. In some embodiments, 3-D printing device is contained in a box that controls temperature and atmosphere. In some embodiments, the atmosphere is modified to adjust the humidly, gas content such as nitrogen purged inside the box. In some embodiments, the box is modified to achieve a vacuum environment.

Figure 37:
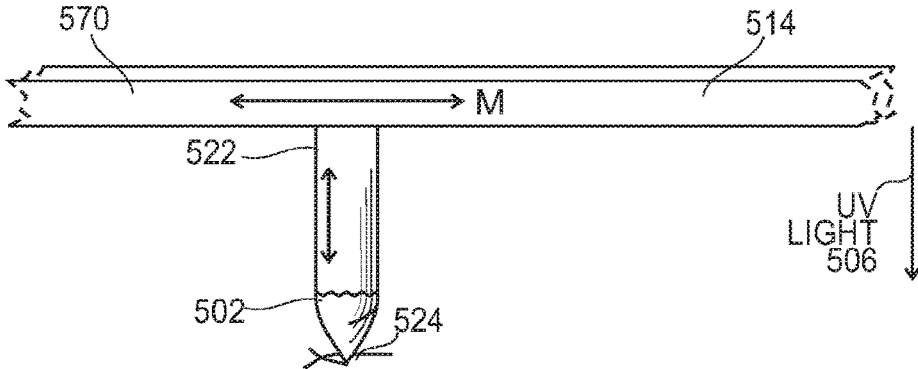
FIG. 37 illustrates a perspective view of an exemplary 3-D printing device according to an aspect of the present application including a source for photolithography.
Figure 38:
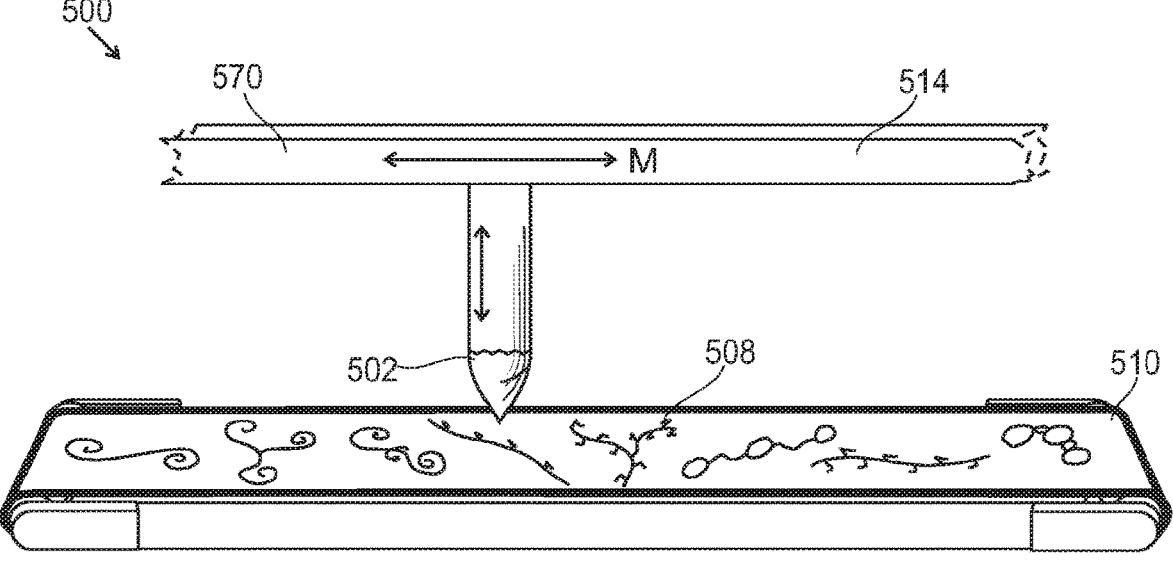
FIG. 38 illustrates a perspective view of an exemplary 3-D printing device according to an aspect of the present application including a moving printing surface.

According to some aspects, 3-D printing device includes a radiation source 506 configured to supply and transfer energy to at least a portion of the powder (e.g., polymer material to make the fiber) applied to the surface. In some embodiments, the radiation source is a laser positioned adjacent to the print head. The laser articulates such that the supplied beam can be focused on selected portions of the printing surface. In some embodiments, the radiation source is an ultraviolet light or other light source used for photolithography. As shown in FIG. 37, the radiation source is configured to be used during or after the print head deposits material (e.g., polymer material) onto the printing surface. The laser beam is focused onto portions of material on the printing surface to melt or sinter the printing materials desired. Once the printed fiber is complete, it may be removed from the residual powdered material left on the printing surface, or the residual powdered material is brushed away. In some embodiments, the laser is focused at a point adjacent to the opening to sinter the material as it is deposited onto the printing surface. Such embodiments may facilitate the elimination of waste since the majority of material extruded onto the printing surface is sintered.

In some embodiments, the laser may include any wavelength of visible light or UV light. In some embodiments, the laser emits alternative forms of radiation, such as, for example, microwave, ultrasound or radio frequency radiation. In some embodiments, the laser is configured to be focused on a portion of printing surface to sinter the printing material deposited thereon. The laser may be emitted in a beam having a small diameter. For example, the diameter of the beam may be between about 0.01 mm and about 0.8 mm. In some embodiments, the diameter of the beam may be between about 0.1 mm and about 0.4 min. In some embodiments, the diameter of the beam is adjustable to customize the intensity of the sintering. In some embodiments, the printing material is deposited on the printing surface and the print head removes by, for example, heating material to remove unwanted printing material from the printing surface to make the implant. The printing material remaining on the printing surface after removal of the unwanted material will be the fiber, the implant, or the implant material.

Figure 30:
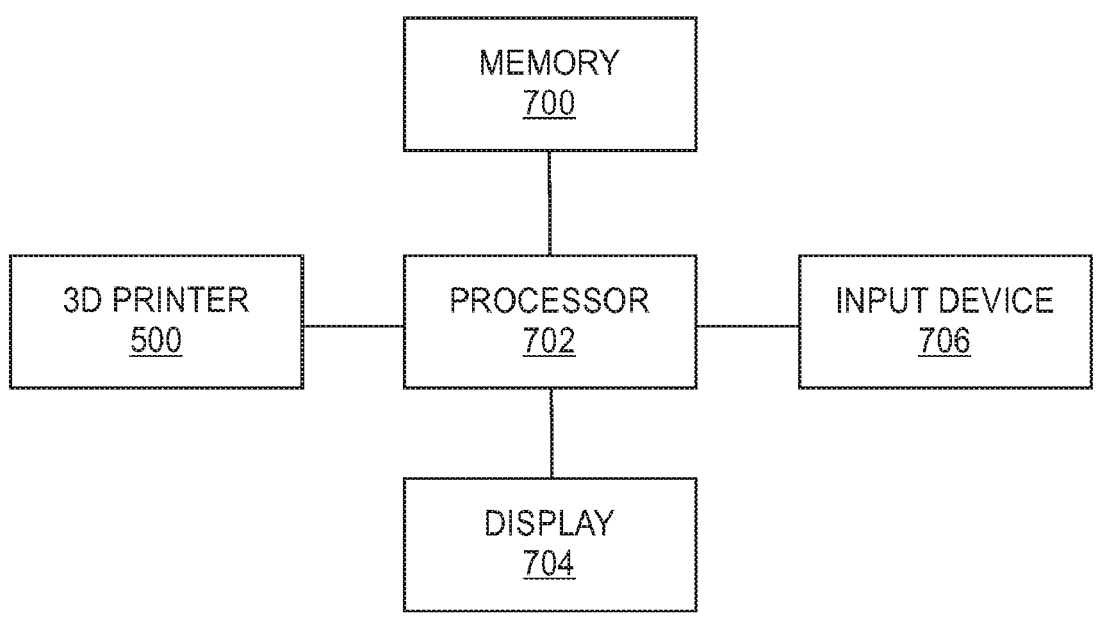
FIG. 30 illustrates an embodiment of a computer-implemented system for producing a fiber of an implantable composition.

In other aspects, as illustrated in FIG. 30, the 3-D printing device includes a controller or processor 702 to accept instructions and automatically manufacture the implantable composition, such as, for example, a fiber, or a coherent mass of fibers having the binding surface, based on the instructions. The fibers can comprise a biodegradable polymer, bone material and a bioactive agent. In some embodiments, the processor comprises memory 700 for temporary or permanent storage of instructions. Various instructions may be programmed and stored in the memory to make multiple designs of the implantable composition and/or the fibers for the implantable composition. In some embodiments, the 3-D printing device includes an input device 706, such as, for example, a keyboard to input commands and instructions. In some embodiments, the processor of the 3-D printing device is configured to receive commands and instructions from an external computer. For example, various instructions may be stored and executed locally on an external computer to operate the 3-D printing device. In some embodiments, the computer and 3-D printing device can be one single device with component parts.

In some embodiments, the processor comprises logic to execute one or more instructions for the computer system to perform a task (for example, to transmit instructions to the 3-D printer, etc.). The logic for executing instructions may be encoded in one or more tangible media for execution by the processor. For example, the processor may execute codes stored in a computer-readable medium such as the memory. The computer-readable medium may be stored in, for example, electronic (for example, RAM (random access memory), ROM (read-only memory), EPROM (erasable programmable read-only memory), magnetic, optical (for example, CD (compact disc), DVD (digital video disc), hard disk drive (HUD), floppy drive, zip drive, compact disk-ROM, bubble memory, flash drive, redundant array of independent disks (RAID), network accessible storage (NAS) systems, storage area network (SAN) systems, electromagnetic, semiconductor technology, or any other suitable medium). CAS (content addressed storage) may also be one or more memory devices embedded within a CPU, or shared with one or more of the other components, and may be deployed locally or remotely relative to one or more components interacting with the memory or one or more modules.

In some embodiments, the instructions include dimensions of the implantable composition (e.g., fibers) to be made. For example, the instructions may include programming as to the length and thickness of the implantable composition. The processor carries out the instructions by causing movement of the base relative to the print head while the printing material is applied to the printing surface. Additionally, the processor may cause movement of the print head in a direction away from the printing surface to allow for a thicker layer of printing material, according to the predetermined specifications in the instructions. In some embodiments, the processor is configured to provide a single layer of the printing material to make the implantable composition. The layer of the material deposited onto the printing surface may have uniform thicknesses or may include varied thicknesses, such as thickness gradients across the length of the implantable composition. In some embodiments, the dimensions of the implantable composition (e.g., fibers) may range from about 0.01 mm to about 1 meter in length, or from about 0.01 mm to about 0.25 mm in length, or from about 0.25 mm to 0.5 mm in length, from about 3 cm to about 8 cm in length, from about 0.01 mm to about 0.25 mm in thickness, or from about 0.25 mm to 0.5 mm in thickness, from about 2 mm to about 30 mm in thickness, or from about 2 mm to about 10 mm in thickness, and from about 2 mm to about 30 mm in width, or from about 2 mm to about 10 mm in width, from about 0.01 mm to about 0.25 mm in width, or from about 0.25 mm to 0.5 mm in width.

Once the processor receives the instructions, the processor directs the 3-D printing device to make the implantable composition based on the received instructions. In some embodiments, the processor directs the lateral movement of the printing surface, and the movement of the print head transverse to the printing surface. In some embodiments, the processor also controls the direction of movement, the movement and the speed of the printing surface. In some embodiments, the processor moves, focuses and directs the laser to emit radiation at a predetermined point on the printing surface. In some embodiments, the processor directs the temperature control unit to heat or cool the printing surface. Based on the instructions received, the processor coordinates simultaneous and/or ordered movement of the base, the printing surface, and the print head relative to one another. The processor also controls the application of the printing material onto the printing surface. For example, the processor directs the pressure at which the printing material is released onto the printing surface. The processor also directs the patterns of application onto the printing surface, including portions where the printing material is not applied to the printing surface to reduce waste. The processor may also direct the laser to emit radiation, such as for example, focused beams of light, in controlled pulses to sinter preselected portions of the printing material on the printing surface. In some embodiments, the processor directs motors which control the movement and rotation of at least the base, the printing surface, and the print head relative to one another. In some embodiments, the processor directs coarse and/or fine movement of components of the 3-D printing device.

Although the components of the system of FIG. 30 are shown as separate modules, they may be combined in one or more computer systems. Indeed, there may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed, Indeed, even a single general purpose computer (or other processor-controlled device) executing a program stored on an article of manufacture (for example, recording medium or other memory units) to produce the functionality referred to herein may be utilized to implement the illustrated embodiments. It also will be understood that the plurality of computers or servers can be used to allow the system to be a network based system having a plurality of computers linked to each other over the network or Internet or the plurality of computers can be connected to each other to transmit, edit, and receive data via cloud computers or in a data drop box.

The computer (for example, memory, processor, storage component, etc.) may be accessed by authorized users, Authorized users may include at least one engineer, technician, surgeon, physician, nurse, and/or health care provider, manufacturer, etc.

The user can interface with the computer via a user interface that may include one or more display devices 704 (for example, CRT, LCD, or other known displays) or other output devices (for example, a printer, etc.), and one or more input devices (for example, keyboard, mouse, stylus, touch screen interface, or other known input mechanisms) for facilitating interaction of a user with the system via user interface. The user interface may be directly coupled to database or directly coupled to a network server system via the Internet, Wi-Fi or cloud computing. In accordance with one embodiment, one or more user interfaces are provided as part of (or in conjunction with) the illustrated systems to permit users to interact with the systems.

The user interface device may be implemented as a graphical user interface (GUI) containing display or the like, or may be a link to other user input/output devices known in the art. Individual ones of a plurality of devices (for example, network/stand-alone computers, personal digital assistants (PDAs), WebTV (or other Internet-only) terminals, set-top boxes, cellular phones, screen phones, pagers, Blackberry, smart phones, iPhone, iPad, table, peer/non-peer technologies, kiosks, or other known (wired or wireless) communication devices, etc.) may similarly be used to execute one or more computer programs (for example, universal Internet browser programs, dedicated interface programs, etc.) to allow users to interface with the systems in the manner described. Database hardware and software can be developed for access by users through personal computers, mainframes, and other processor-based devices, Users may access and data stored locally on hard drives, CD-ROMs, stored on network storage devices through a local area network, or stored on remote database systems through one or more disparate network paths (for example, the Internet).

The database may include a data storage device, a collection component for collecting information from users or other computers into a centralized database, a tracking component for tracking information received and entered, a search component to search information in the database or other databases, a receiving component to receive a specific query from a user interface, and an accessing component to access centralized database. A receiving component is programmed for receiving a specific query from one of a plurality of users. The database may also include a processing component for searching and processing received queries against a data storage device containing a variety of information collected by a collection device.

The disclosed system may, in some embodiments, be a computer network based system. The computer network may take any wired/wireless form of known connective technology (for example, corporate or individual LAN, enterprise WAN, intranet, Internet, Virtual Private Network (VPN), combinations of network systems, etc.) to allow a server to provide local/remote information and control data to/from other locations (for example, other remote database servers, remote databases, network servers/user interfaces, etc.). In accordance with one embodiment, a network server may be serving one or more users over a collection of remote and disparate networks (for example, Internet, intranet, VPN, cable, special high-speed ISDN lines, e The network may comprise one or more interfaces (for example, cards, adapters, ports) for receiving data, transmitting data to other network devices, and forwarding received data to internal components of the system (for example, 3-D printers, print heads, etc.).

In accordance with one embodiment of the present application, the data may be downloaded in one or more textual/graphical formats (for example, RTF, PDF, TIFF, JPEG, STL, XML, XDFL, TXT etc.), or set for alternative delivery to one or more specified locations (for example, via e-mail) in any desired format (for example, print, storage on electronic media and/or computer readable storage media such as CD-ROM, etc.). The user may view the search results and underlying documents at the user interface, which allows viewing of one or more documents on the same display.

Methods of Making an Implantable Composition

Figure 31:
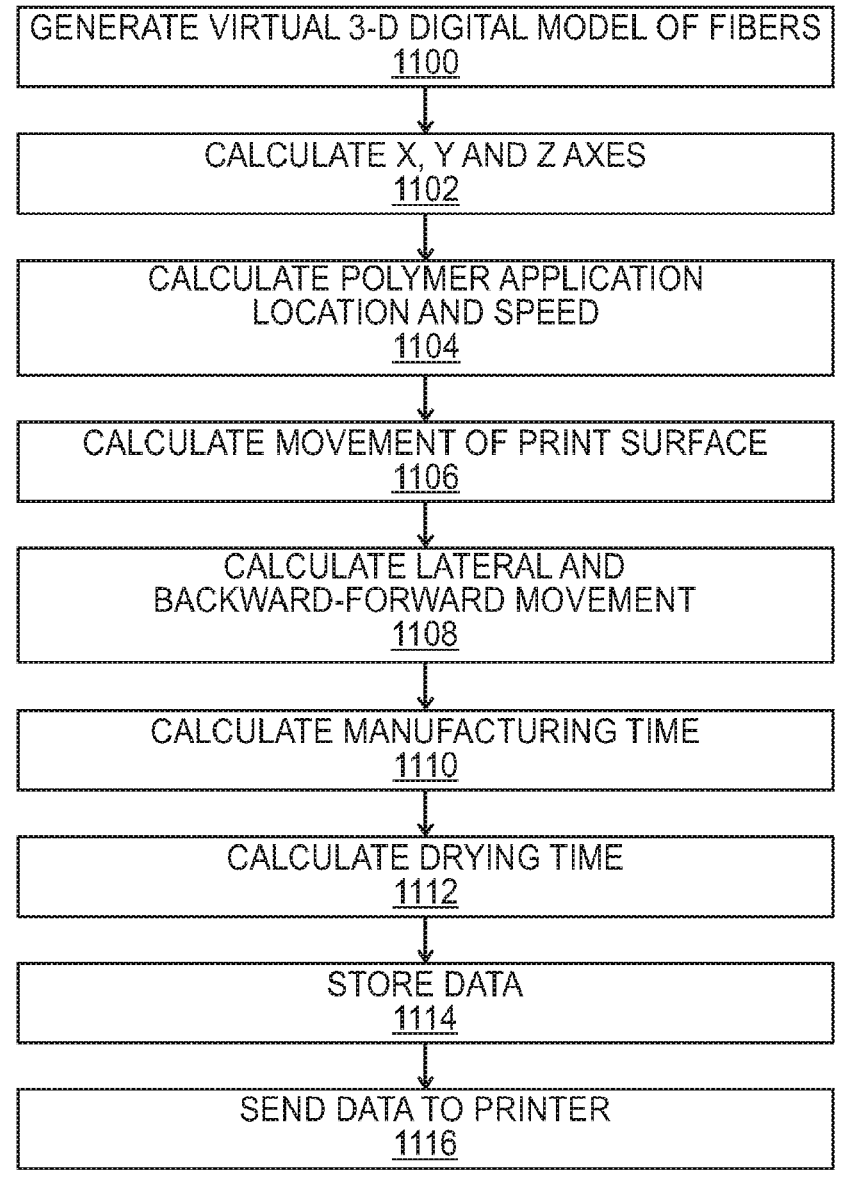
FIG. 31 is a flow diagram illustrating an embodiment of the computer-implemented system that the processor performs for producing a fiber of an implantable composition.

As shown in FIG. 31, a computer implemented method for producing the implantable composition is illustrated. In a first step 1100, a user or a designer generates a virtual image of the object or a 3-D digital model to be created with the 3-D printing machine, such as, for example, the implantable composition including a fiber having a binding surface and a non-binding surface and a virtual depth, thickness and volume of the implantable composition. The computer can generate a virtual 3-D image of the implantable composition including a virtual volume, length, and width of the fiber to be printed. Commercially available CAM software can make the CAD drawing/design of the implantable composition into computer code, (for example, g-code). This code is sent to the device and the controller controls the device and the loading of the print head with the printing material, the heating and cooling temperature and time of the printing material, laser emit time, rotation, movement speed of the printing surface, the print head, the table, lateral movement of the printing surface, the print head, and the table as well as other parameters. The controller device creates a medical implant from or in the material based on the 3-D digital model. In some embodiments the 3-D digital model of the implantable composition is generated based on the 3-D image of an intended bone repair site. The 3-D image of a bone repair site can be obtained by using (i) one or more X-ray images; (ii) a computer aided design (CAD) program; (iii) a cone beam imaging device; (iv) a computed tomography (CT) scan device; (v) a magnetic resonance imaging (MRI); (vi) 3-D laser camera, or a combination thereof.

In a second step 1102, the processor calculates the X, Y, and Z axes. The device employs Cartesian coordinate system (X, Y, Z) for 3-D motion control and optionally employs a 4th axis ($A_1$) for the movement of the printing surface (for example, 360 degrees) relative to the print head. The implant can be designed virtually in the computer with a CAD/CAM program, which is on a computer display. The user inputs specific parameters into the computer and then presses print on the display to start the 3-D printing manufacturing. The computer logic programs the computer with instructions for loading of the print head with the printing material; application and thickness of the polymer from the print head; the heating and cooling temperature and time of the device; laser emit time; rotation; movement speed of the printing surface, the print head, and/or the table; and/or lateral movement of the printing surface, the print head, and/or the table as well as other parameters in accordance with the received instructions. The controller device causes the print head to be located at the appropriate X, Y, Z coordinates for 3-D motion control and optionally employs a 4th axis ($A_1$) for the rotation of the printing surface (for example; 360 degrees, 180 degrees, 120 degrees) relative to the print head to print the implantable composition (e.g., fiber). After the implantable composition is produced on all or a portion of the printing surface, it can be removed by a tool that engages the printing surface. In some embodiments, the device can have a tool to etch, shape, and/or dry the implant before, during or after it is removed from the printing surface.

In a third step 1104, the processor calculates the polymer application location and speed by planning coordination of the printing surface and the print head. In some embodiments, the current device does not manufacture the implantable composition by printing the printing material in successive layers to form the implantable composition. In a fourth step 1106 and a fifth step 1108, processor 102 calculates the overall and rotational movement of the printing surface and the lateral and/or backward and forward movement of the printing surface and the print head. In some embodiments, the printing surface of the current application has the polymer continuously dispensed from the print head and onto the printing surface as the printing surface rotates in 360 degrees clockwise and/or counterclockwise relative to the print head and the table, and/or the printing surface can, in some embodiments, move in a forward, lateral, and/or backward direction so that the fibers to make the implantable composition are formed in accordance with the instructions received from the computer. In some embodiments, the printing surface of the current application has a heat sensitive polymer disposed on it and then the print head receives instructions to heat the surface area to be removed (for example, by laser, heating element, or the like). In this way, fibers of the polymer are made by removing the heated portions of the polymer and what is left on the printing surface are fibers for the implantable composition. The printing surface rotates 360 degrees clockwise and/or counterclockwise directions relative to the print head and the table and/or the printing surface. In some embodiments, the printing surface can move in a forward, lateral, and/or backward direction so that the fibers used to make the implantable composition are formed as the rest of the polymer is removed from the printing surface in accordance with the instructions received from the computer.

In some embodiments, the printing surface of the current application has the polymer in dry powder form continuously dispensed from the print head and onto the printing surface as the printing surface rotates in 360 degrees clockwise and/or counterclockwise relative to the print head and the table, and/or the printing surface can, in some embodiments, move in a forward, lateral, and/or backward direction so that fibers used to make the implantable composition are formed in accordance with the instructions received from the computer. After, the powder application, which can be from the print head from a reservoir therein, the print head (for example, a laser or heating element coupled thereto) can heat the powder polymer and form the fibers for the implantable composition.

Based on the above calculations, the processor calculates a projected amount of time it will take to manufacture the implantable composition in step 1110. In a subsequent step 1112, the processor calculates the amount of time it will take for the printed medical device to dry. In some embodiments, the printing material applied to the printing surface is temperature sensitive and dries and/or cures through heating or cooling. In some embodiments, the processor directs the temperature control unit to heat or cool the printing surface. In some embodiments, the processor directs the laser to focus its beam on the printing material applied to the printing surface to sinter and cure the printing material.

In step 1114, the data calculated by the processor is stored in the memory for subsequent implementation. In some embodiments, the processor processes and organizes the calculated data into the memory. In some embodiments, the processor includes value-determining logic, development logic, security logic, and/or analytical logic. In some embodiments, the processor updates the memory with any new calculation data received from the user. In some embodiments, there is a computer readable storage medium storing instructions that, when executed by a computer, cause the computer to display options for a user to enter, view, and edit some or all features for manufacturing the implant including the loading of the print head with the printing material; the heating and cooling temperature and time of the printing material; laser emit time; rotation angle; movement speed of the printing surface, the print head and/or the table; lateral movement of the printing surface, the print head and the table; as well as other parameters. The controller device creates a medical implant from or in the printing material by instructions received from the computer. In some embodiments, the device employs Cartesian coordinate system (X, Y, Z) for 3-D motion control and optionally employs a 4th axis ($A_1$) for the rotation of the printing surface (for example, 360 degrees) relative to the print head.

In a final step 1116, the user inputs a command to send the stored data to the printer to create the medical device. The user inputs specific parameters into the computer and then presses print on the display to start the 3-D printing manufacturing. The computer logic causes the computer to execute loading of the print head with the printing material; the heating and cooling temperature and time of the device; laser emit time; rotation; movement speed of the printing surface, the print head, and/or the table; and/or lateral movement of the printing surface, the print head, and/or the table; as well as other parameters. The controller device causes the print head to be located at the appropriate X, Y, Z coordinates for 3-D motion control and optionally employs a 4th axis ($A_1$) for the rotation of the printing surface (for example, 360 degrees, 180 degrees, 120 degrees) relative to the print head to make the implantable composition (e.g., single fiber, multiple fibers, coherent mass, etc.) from or in the printing material.

Figure 32:
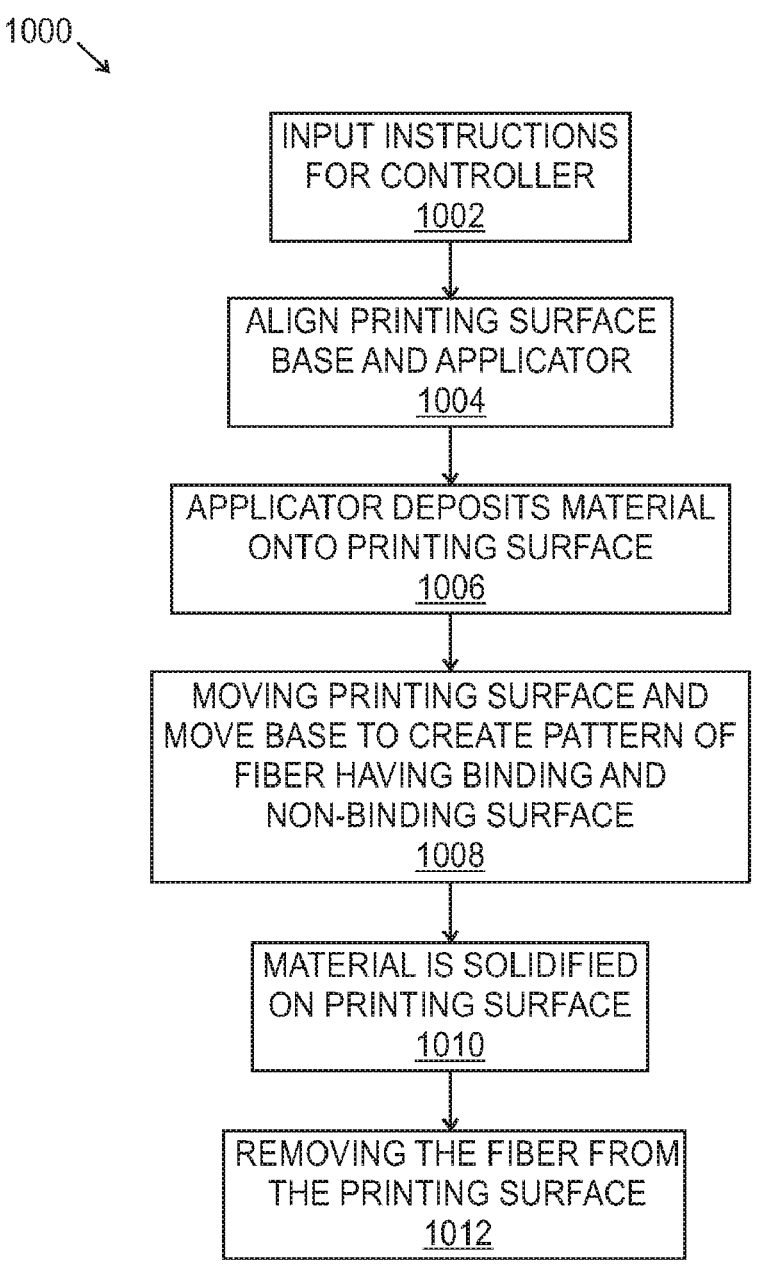
FIG. 32 is a flow diagram illustrating an embodiment of the computer-implemented system that the processor performs for producing a fiber of an implantable composition, through the use of a 3-D printing machine having a moving printing surface.
Figure 35:
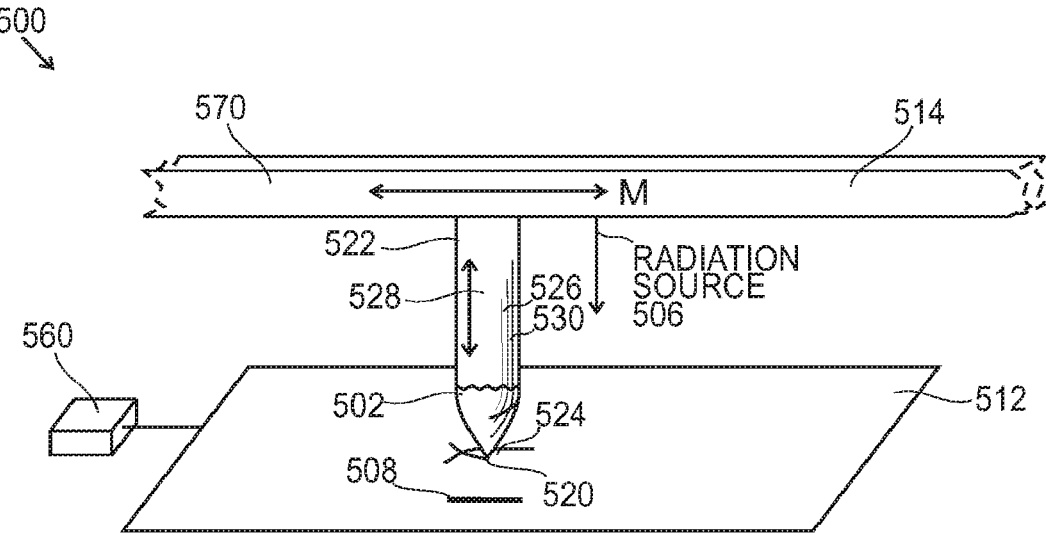
FIG. 35 illustrates a perspective view of an exemplary 3-D printing device according to an aspect of the present application.
Figure 36:
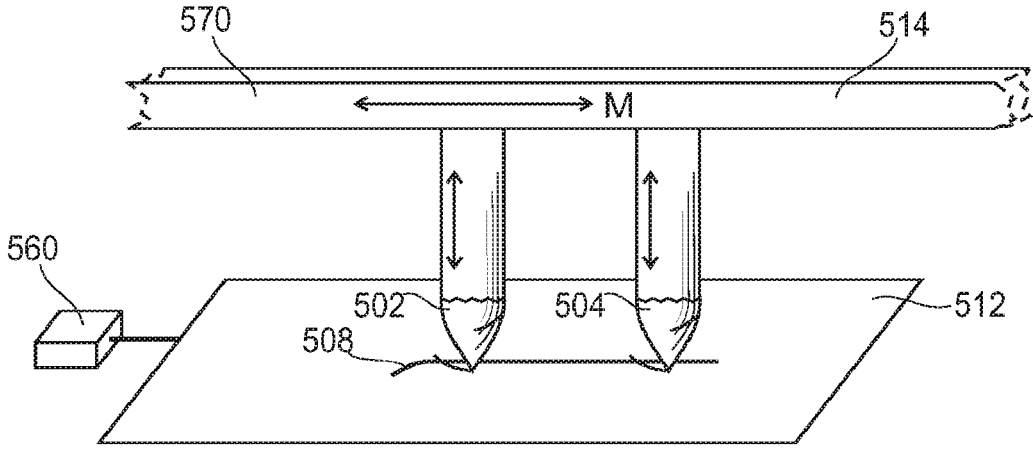
FIG. 36 illustrates a perspective view of an exemplary 3-D printing device according to an aspect of the present application including multiple print head.

In various embodiments as shown in FIGS. 32, a computer implemented method 1000 of fabricating a fiber of the implantable composition, through use of a 3-D printing device is provided. In some embodiments, the method includes step 1002 for inputting instructions for a computer processor to carry out the manufacture, step 1004 for aligning the printing surface, the base and the print head relative to one another, step 1006 for depositing printing material onto the printing surface, step 1008 for moving the printing surface and moving the base to create a pattern of a fiber having binding and/or non-binding surfaces, step 1010 for solidifying the printing material on the printing surface, and step 1012 for removing the desired 3-D printed implantable composition including fibers. In some embodiments, the method comprises moving a print surface in alternating clockwise and counterclockwise directions, ejecting material from a print head to the print surface to make a strand having a wave-like pattern with alternating peaks and crests, and rotating the print head such an angular distance to create a plurality of interconnected threads on the printing surface.

In other embodiments, the processor receives instructions for the manufacture of the implantable composition. A user may input instructions directly into the 3-D printing device and input instructions into an external computer in communication with the processor. According to various aspects, a user loads a material reservoir (not shown) in communication with the print head with a suitable material. The printing material may be in liquid form, particulate form, gel form, or solid form. The processor moves the printing surface and one or more print heads into place relative to one another. Once positioned, the print head begins to deposit the printing material onto the printing surface. In some embodiments, the print head continuously deposits the material as the printing surface is rotated and/or moved laterally along the x-y plane. In some embodiments, the printing surface is rotated in the clockwise and counterclockwise directions while the base moves laterally to form wave-shaped threads. The degree of rotation may be adjusted to impart flexible and stretchable qualities onto each of the formed the implantable composition. For example, the implantable composition having shorter wavelengths will be able to be stretched more than the implantable composition having longer wavelengths. In some embodiments, the processor directs rotation of the printing surface and lateral movement of base to impart stretchability of the implantable composition that is uniform across its length. In some embodiments, the processor directs variable rotation of the printing surface and lateral movement of the base such that the implantable composition includes regions of increased stretchability according to the needs of a surgical application.

The movement of the base, the printing surface and the print head relative to one another and the application of the printing material onto the printing surface is repeated a number of times such that the implantable composition encompasses the surface of the printing surface. That is, each time the implantable composition having a wave-like shape is applied to the printing surface, a similar implantable composition is applied to the printing surface adjacent to the first thread. In some embodiments, the implantable compositions are extruded adjacent to one another, such that the peaks of a first set of fibers of the implantable composition are extruded to contact the crest of an adjacent second set of fibers of the implantable composition. In some embodiments, the implantable composition may be created entirely from fibers having this configuration. It will be understood that, in some embodiments, the fiber printed will be a layered fiber.

In some embodiments, the print head deposits the printing material in powdered form onto the printing surface. The printing material can be sintered and/or melted to form the implantable composition. In some embodiments, a radiation source, such as a laser may be used in conjunction with the print head. The processor directs the laser to be focused at a point on which the printing material has been deposited adjacent the print head. The processor also provides power to the laser during desired intervals to prevent unwanted damage to the implantable composition and/or the printing surface according to the instructions. That is, the laser will emit a beam while sintering material to create the desired fibers, but will not emit a beam when the printing surface is being repositioned relative to the print head. Once all desired sintering has been completed, any excess material may be brushed away from the printing surface to be discarded or recycled.

In some embodiments, the printing material may be sintered through use of the temperature control unit (e.g., a heating unit). The temperature control unit provides energy to the printing surface such that the powdered material melts and molds together. An amount of heat may be provided such that the material melts quickly upon contact with the printing surface.

In some embodiments, the printing surface is heated or cooled using the temperature control unit to remove the implantable composition. In some embodiments, the printing surface may be removed from the 3-D printing device and submerged in a solvent to loosen and remove the implantable composition.

FIG. 33 is a flow diagram of representative steps of a computer implemented method of producing a custom implantable composition 1200. The method includes step 1202 for obtaining a 3-D image of the implant location or intended bone repair site, including the topography of the bone repair site or the implantable composition, or the location of the implantable composition. Step 1202 can be accomplished by using many known techniques of obtaining a 3-D image including, but not limited to, (i) one or more X-ray images; (ii) a computer aided design (CAD) program; (iii) a cone beam imaging device; (iv) a computed tomography (CT) scan device; (v) a magnetic resonance imaging (MRI); or a combination thereof. In step 1204, the images obtained in step 1202 may be input into a suitable digital data processor to create a 3-D model of a custom implantable composition. In step 1206, osteogenic material including, in some cases, polymers that preserve the biological activity of demineralized bone particles and/or fibers and have a load bearing structure, are supplied to form ink that can be used in steps 1208 and 1209. The load bearing structure, in some aspects, can be a metal or non-metal structure. In step 1208, the 3-D printer may first check to determine if the final as printed all the layers required to produce the custom implantable composition.

These layers may have been provided by a programmed module operative on a digital data processing device and may be the 3-D model of the custom implantable composition reduced to consecutive slices, that when printed in the correct order, may result in the desired implantable composition.

In step 1209, the 3-D printer may print the next layer if the final layer has not yet been printed. This may be done, for instance, by moving the print nozzle in a raster fashion, depositing ink where required. The printing is performed in a sterilized environment.

In step 1210, once the 3-D printer has printed all the required layers that constitute the custom implantable composition, the implantable composition may undergo post-print processing. This post-processing step may, for instance, include actions such as, but not limited to, dissolving out the sucrose crystals, if any are present, to provide a porous structure and sterilization of the custom implantable composition.

In some embodiments, each process produces a fiber of the implantable composition. The process is repeated until a sufficient amount of fibers are printed. In step 1212, the fibers are processed to be collected and ready to be molded, in some embodiments via mechanical entanglement. The amount of the fibers needed are calculated based on the 3-D model of the implantable composition. In step 1214, the fibers are molded into a coherent mass having desired characteristics and the shape according to the 3-D image of the implant location. In step 1216, the final form of the coherent mass is the 3-D printed custom implantable composition, which is inserted into the patient at the intended bone repair site.

FIG. 34 is a flow diagram illustrating representative steps that the logic performs for producing the implantable composition according to an embodiment of this application 1300. The computer is programmed for 3-D printing of the implantable composition by obtaining a 3-D image of an intended bone repair site. This can be done by taking one or more X-ray images, using a computer aided design (CAD) program, a cone beam imaging device, a computed tomography (CT) scan device, or a magnetic resonance imaging (MRI). The image can then be scanned or input into the computer system similar to step 1202. A 3-D digital model of the intended bone repair site is generated based on step 1302 of selecting a general shape of the fiber including the geometry of the body portion, and/or end portion, and/or edge portion. In some embodiments, the 3-D model is also based on step 1304 of selecting a shape type of binding surface of the fiber including curled, branched, helical and other geometry as discussed above. In some embodiments, the step 1306 further includes determining the dispositions of a binding surface and a non-binding surface on the fiber. Based on the 3-D image and the 3-D digital model including a virtual depth, thickness and volume of the intended bone repair site, a 3-D digital model of the custom implantable composition including the fibers is generated in step 1308. For example, if the intended bone repair site has a bone defect, the computer will generate a virtual 3-D model of the implantable composition, including a virtual depth, thickness and volume of the implantable composition, that can fit within the bone defect. Thus, a variety of 3-D models of the implantable composition can be generated that will fit within the bone defect. In some embodiments, the computer will create a variety of shapes and sizes of the implantable composition that will fit within the bone defect and the user can select the desired shape. In this way, a custom implantable composition can be selected. The computer will store the digital models in step 1308 on the database.

The computer processor will have instructions to retrieve the stored 3-D digital model of the implantable composition and select appropriate printing material including bone materials for the 3-D digital model of the implantable composition in step 1310. Thus, the computer will control the amount of bone material and/or carrier used in the printing process, either in one or more printing heads, to print the implantable composition. In some embodiments, the carrier is not a wetting agent to mold or hold the coherent mass together. The carrier is an ink that fills the printer, which can include the polymer, a bioactive agent, bone material or a combination therefore used to manufacture the implantable composition. For example, osteogenic material including, in some cases, a polymer that preserves the biological activity of demineralized bone particles and/or fibers can be supplied to form the ink that can be used in the printing step. In step 1312, the computer further selects a printing method including additive and subtractive manufacturing. In step 1314, the computer further selects a desired process based on the user's need including a batch process or a continuous process. In step 1316, the 3-D printer is based on a programmed module operative on a digital data processing device and may generate the desired fiber according to the selected geometry of 3-D model, printing method and printing process.

In some embodiments, the implantable composition requires a plurality of fibers. In some embodiments, the plurality of fibers is removed from the printing surface and is molded into the desired implantable composition according to the 3-D model. In some embodiments, the printing may be performed in a sterilized environment. In some embodiments, the process, as illustrated in FIGS. 31-34, includes a post processing step and may, for instance, include actions such as, but not limited to, dissolving out the sucrose crystals, if any are present, to provide a porous structure and sterilization of the custom implantable composition.

In various embodiments, a computer implemented method for producing the implantable composition having a fiber is provided. In some embodiments, the fiber has a filamentous structure. The computer implemented method for producing the implantable composition comprising a fiber includes obtaining a 3-D image of an intended bone defect site; generating a 3-D digital model of the implantable composition based on the 3-D image, the 3-D digital model of the implantable composition being configured to fit within the intended bone defect site; storing the 3-D digital model on a database coupled to a processor, the processor having instructions for retrieving the stored 3-D digital model of the implantable composition, and in some embodiments, the processor also having instructions for combining a carrier material with, in or on a material, based on the stored 3-D digital model for instructing a 3-D printer to produce the implantable composition.

In some aspects, the computer implemented method produces the implantable composition by combining the carrier material with the printing material and instructing the 3-D printer to print the implantable composition based on the stored 3-D digital model. In other aspects, the computer implemented method produces the implantable composition by instructing the 3-D printer to print the carrier material and then print the printing material in or on the carrier material based on the stored 3-D digital model. In some embodiments, the carrier material is not required. In yet other embodiments, the computer implemented method produces the implantable composition which is customized to the intended bone repair site.

In certain embodiments, the 3-D image of an intended bone repair site is a computed tomography image of an unhealthy bone repair site, based on a computed tomography image of a healthy bone repair site. In other embodiments, the 3-D image is obtained from (i) one or more X-ray images; (ii) a computer aided design (CAD) program; (iii) a cone beam imaging device; (iv) a computed tomography (CT) scan device; (v) a magnetic resonance imaging (MRI) or a combination thereof.

Generally, in many implementations, the carrier material comprises a biodegradable polymer, a metal, or a combination thereof and the bone material comprises mineralized or demineralized bone.

In some embodiments, the implantable composition includes biodegradable polymers. Exemplary biodegradable materials include lactide-glycolide copolymers of any ratio (e.g., 85:15, 40:60, 30:70, 25:75, or 20:80), poly(L-lactide-co-D,L-lactide), polyglyconate, poly(arylates), poly(anhydrides), poly(hydroxy acids), polyesters, poly(ortho esters), poly(alkylene oxides), polycarbonates, poly(propylene fumarates), poly(propylene glycol-co fumaric acid), poly (caprolactones), polyamides, polyesters, polyethers, polyureas, polyamines, polyamine acids, polyacetals, poly(orthoesters), poly(pyrolic acid), poly(glaxanone), poly (phosphazenes), poly(organophosphazene), polylactides, polyglycolides, poly(dioxanones), polyhydroxybutyrate, polyhydroxyvalyrate, polyhydroxybutyrate/valerate copolymers, polyvinyl pyrrolidone), biodegradable polycyanoacrylates, biodegradable polyurethanes including glucose-based polyurethanes and lysine-based polyurethanes, and polysaccharides (e.g., chitin, starches, celluloses). In certain embodiments, the polymer used in the implantable composition is poly(lactide-co-glycolide). The ratio of lactide and glycolide units in the polymer may vary. Particularly useful ratios are approximately 45-80% lactide to approximately 44-20% glycolide. In certain embodiments, the ratio is approximately 50% lactide to approximately 50% glycolide. In other certain embodiments, the ratio is approximately 65% lactide to approximately 45% glycolide. In other certain embodiments, the ratio is approximately 60% lactide to approximately 40% glycolide. In other certain embodiments, the ratio is approximately 70% lactide to approximately 30% glycolide. In other certain embodiments, the ratio is approximately 75% lactide to approximately 25% glycolide. In certain embodiments, the ratio is approximately 80% lactide to approximately 20% glycolide. In certain of the above embodiments, lactide is D,L-lactide. In other embodiments, lactide is L-lactide. In certain particular embodiments, RESOMER® 824 (poly-L-lactide-co-glycolide) (Boehringer Ingelheim) is used as the polymer in the implantable composition. In certain particular embodiments, RESOMER® 504 (poly-D,L-lactide-co-glycolide) (Boehringer Ingelheim) is used as the polymer in the implantable composition. In certain particular embodiments, PURASORB PLG (75/25 poly-L-lactide-co-glycolide) (Purac Biochem) is used as the polymer in the implantable composition. In certain particular embodiments, PURASORB PG (polyglycolide) (Purac Biochem) is used as the polymer in the implantable composition. In certain embodiments, the polymer is PEGylated-poly(lactide-co-glycolide). In certain embodiments, the polymer is PEGylated-poly(lactide). In certain embodiments, the polymer is PEGylated-poly(glycolide). In other embodiments, the polymer is polyurethane. In other embodiments, the polymer is polycaprolactone.

In certain embodiments, the biodegradable polymer is a copolymer of poly(caprolactone) and poly(lactide). For polyesters such as poly(lactide) and poly(lactide-co-glycolide), the inherent viscosity of the polymer ranges from about 0.4 dL/g to about 5 dL/g. In certain embodiments, the inherent viscosity of the polymer ranges from about 0.6 dL/g to about 2 dL/g. In certain embodiments, the inherent viscosity of the polymer ranges from about 0.6 dL/g to about 3 dL/g. In certain embodiments, the inherent viscosity of the polymer ranges from about 1 dL/g, to about 3 dL/g. In certain embodiments, the inherent viscosity of the polymer ranges from about 0.4 dL/g to about 1 dL/g. For poly (caprolactone), the inherent viscosity of the polymer ranges from about 0.5 dL/g to about 1.5 dL/g. In certain embodiments, the inherent viscosity of the poly(caprolactone) ranges from about 1.0 dL/g to about 1.5 dL/g. In certain embodiments, the inherent viscosity of the poly(caprolactone) ranges from about 1.0 dL/g to about 1.2 dL/g. In certain embodiments, the inherent viscosity of the poly (caprolactone) is about 1.08 dL/g.

Natural polymers, including collagen, polysaccharides, agarose, glycosaminoglycans, alginate, chitin, and chitosan, may also be employed in the ink to make the fiber having a binding surface. Tyrosine-based polymers, including but not limited to polyarylates and polycarbonates, may also be employed (Pulapura, et al., "Tyrosine-derived polycarbonates: Backbone-modified "pseudo"-poly(amino acids)

designed for biomedical applications," *Biopolymers,* 1992, 32: 411-417; Hooper, et al., "Diphenolic monomers derived from the natural amino acid α-L-tyrosine: an evaluation of peptide coupling techniques," *J. Bioactive and Compatible Polymers,* 1995, 10:327-340, the contents of both of which are incorporated herein by reference). Monomers for tyrosine-based polymers may be prepared by reacting an L-tyrosine-derived diphenol compound with phosgene or a diacid (Hooper, 1995; Pulapura, 1992). Similar techniques may be used to prepare amino acid-based monomers of other amino acids having reactive side chains, including imines, amines, thiols, and the like. In one embodiment, the degradation products include bioactive materials, biomolecules, small molecules, or other such materials that participate in metabolic processes.

Polymers may be manipulated to adjust their degradation rates. The degradation rates of polymers are well characterized in the literature (see *Handbook of Biodegradable Polymers,* Domb, et al., eds., Harwood Academic Publishers, 1997, the entire contents of which are incorporated herein by reference). In addition, increasing the cross-link density of a polymer tends to decrease its degradation rate. The cross-link density of a polymer may be manipulated during polymerization by adding a cross-linking agent or promoter. After polymerization, cross-linking may be increased by exposure to UV light or other radiation. Co-monomers or mixtures of polymers, for example, lactide and glycolide polymers, may be employed to manipulate both degradation rate and mechanical properties.

In some embodiments, the implantable composition comprises biodegradable polymeric or non-polymeric material. In some embodiments, the biodegradable polymer may provide immediate release or sustained release of the biologically active material. For example, the biodegradable polymer comprises polyether ether ketone (PEEK). In some embodiments, the implantable composition may comprise one or more poly (alpha-hydroxy acids), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrroli done, polyvinyl alcohol (PVA), PVA-g-PLGA, PELT-PBT copolymer (polyactive), methacrylates, PEO-PPO-PAA copolymers, PLGA-PEO-PLGA, PEG-PLG, PLA-PLGA, poloxamer 407, PEG-PI-GA-PEG triblock copolymers, POE, SAM (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, chitosan, or combinations thereof.

In some embodiments, the implantable composition may not be fully biodegradable. For example, the implantable composition may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof. Typically, these types of matrices may need to be removed after a certain amount of time.

In various embodiments, the particle size distribution of the biodegradable polymer may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In sonic embodiments, at least 95% of the particles have a size from about 20 micrometers to about 180 micrometers. In some embodiments, all of the particles have a size from about 20 micrometers to about 180 micrometers.

In some embodiments, the implantable composition comprises one or more polymers (e.g., PLA, PLGA, etc.) having a MW of from about 15,000 to about 150,000 Da or from about 25,000 to about 100,000 Da.

In some embodiments, the implantable composition comprises at least one biodegradable material in a wt % of from about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, to about 5% based on the total weight of the implantable composition. In some embodiments, the biodegradable polymer comprises a range of about 0.1% to about 20% based on the total weight of the implantable composition. In some embodiments, the biodegradable polymer comprises a range of about 0.1% to about 15% based on the total weight of the implantable composition. In some embodiments, the biodegradable polymer comprises 14%, 13%, 12%, 11%, 10%, 9%, 8%, 7%, 6%, or 5% based on the total weight of the implantable composition.

In some embodiments, the biodegradable polymer is present in an amount of about 0.01% to about 50 wt % or about 8.0 wt % to about 50 wt % of the implantable composition. In some embodiments, the biodegradable polymer is present in an amount of about 0.1 wt % to about 10 wt %, about 10 wt % to about 20 wt %, about 20 wt % to about 30 wt %, about 30 wt % to about 40 wt %, or about 40 wt % to about 50 wt %. In other embodiments, the biodegradable polymer comprises 0.2 to 2% and the ceramic particles about 98 to 99.8% by weight of the implantable composition.

Mannitol, trehalose, dextran, mPEG and/or PEG may be used as a plasticizer for the polymer. In some embodiments, the polymer and/or plasticizer may also be coated on the implantable composition to provide a desired release profile.

In various embodiments, the carrier material can be a metal, for example a biodegradable metal. The term "biodegradable metal" (BM) has been generally used to describe degradable metallic biomaterials for medical applications. Useful biodegradable metals include without limitation magnesium based BMs including pure magnesium, magnesium-calcium alloy, magnesium zinc alloy and iron based BMs include pure iron, iron manganese alloys.

In another embodiment, a magnesium alloy may include from about 90 to about 98 weight % magnesium, from about 0 to about 6 weight % aluminum, from about 0 to about 2 weight 0 zinc, and from about 0 to about 3% rare earth metal(s). In another embodiment, the magnesium alloy may be AE42, which includes 94 weight % magnesium, 4 weight % aluminum, and 2 weight % rare earth metal(s).

In various implementations, the bone material used for the computer implemented method for producing the implantable composition and which can be used with a 3-D printer includes allograft, demineralized bone matrix fiber, demineralized bone chips or a combination thereof.

In accordance with some embodiments, the carrier material used to make the fiber, which may optionally contain a bone material, may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; anti-microbials and/or antibiotics such as erythromycin, bacitracin, neomycin, penicillin, polymyxin B, tetracyclines, biomycin, chloromycetin, and streptomycins, cefazolin, ampicillin, azactarn, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anticholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug, a growth factor, a protein or a combination thereof. In some embodiments, the bioactive agent may be a growth factor, cytokine, extracellular matrix molecule, or a fragment or derivative thereof, for example, a protein or peptide sequence such as RGD.

In some embodiments, the polymer may have a modulus of elasticity in the range of from about $1\times10^2$ dynes/cm$^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

Method of Treating a Bone Defect

Accordingly, in some implementations, this application also provides a method of treating a bone defect in a patient, the method comprising administering an implantable composition comprising 3-D printed fibers to the intended bone defect, wherein the fibers are mechanically binded without an additional binding agent. In other implementations, the method of treatment comprises administering an implantable composition to the intended bone defect, wherein the 3-D printed fibers comprise a biodegradable polymer, a bone material and a bioactive agent.

In some embodiments, a method of treating a bone or soft tissue defect is provided. The method comprises inserting an implantable composition into the bone or soft tissue defect, the implantable composition comprising a first set of fibers and a second set of fibers, the first set of fibers comprising a first binding surface and a first non-binding surface, the second set of fibers comprising a second binding surface and a second non-binding surface, the first binding surface of the first set of fibers bound to at least at or near the second binding surface of the second set of fibers and the second set of fibers bound to at least at or near the first binding surface of the first set of fibers.

In some embodiments, the first binding surface of the first set of fibers comprises a curl portion, a hook portion, a branched portion, a barbed portion, a looped portion, a chain portion, a helical portion, a spiral portion, an angular portion, a twist portion, a ribbon portion, a sinusoidal portion, or a zigzag portion and the second binding surface of the second set of fibers also comprises a curl portion, a hook portion, a branched portion, a barbed portion, a looped portion, a chain portion, a helical portion, a spiral portion, an angular portion, a twist portion, a ribbon portion, a sinusoidal portion, or a zigzag portion.

In some embodiments, the first non-binding surface of the first set of fibers comprises a straight portion and the second non-binding surface of the second set of fibers also comprises a straight portion and the implantable composition is a bone void filler.

In some embodiments, the first set of fibers and the second set of fibers comprise a resorbable polymer, a non-resorbable polymer, an ink of organic material, an ink of synthetic material, a therapeutic agent, a soft tissue, a bone material or a combination thereof.

For placement, the substance or substances may be provided in the implantable composition and placed in vivo, for example, at a bone defect. In one embodiment, the implantable composition is placed in vivo by placing the implantable composition in a catheter or tubular inserter and delivering the implantable composition with the catheter or tubular inserter. The implantable composition, with a substance provided therein, may be steerable such that it can be used with flexible introducer instruments for, for example, minimally invasive spinal procedures. For example, the implantable composition may be introduced down a tubular retractor or scope, during XLIF, TLIF, or other procedures.

In clinical use, a delivery system comprising an implantable composition and delivered substance may be used in any type of spinal fusion procedure including, for example, posterolateral fusion, interbody fusion (of any type), facet fusion, spinous process fusion, anterior only fusion, or other fusion procedure. Examples of such spinal procedures include posterior lumbar interbody fusion (PLIF), anterior lumbar fusion (ALIF) or posterior cervical or cervical interbody fusion approaches. In some embodiments, the implantable composition useful with TLIF, ALIT or XLIF procedures may be tubular and have dimensions of approximately 2.5 cm in length and approximately 0.5 cm in width. In other ALIF procedures, the implantable composition of approximately 1 cm by 1 cm can be used. In various embodiments, the implantable composition may be tubular and may have dimensions of approximately 5 mm to approximately 10 mm long and approximately 0.5 cm to 1 cm wide. In other embodiments, the implantable composition (with or without substance loaded) may be placed in a cage, for example, for interbody fusion.

In some embodiments, the 3-D printed implantable composition may be incorporated with a substance before printing or incorporated by the surgeon. In various embodiments, the 3-D printed implantable composition conforms to surrounding bony contours when implanted in vivo.

The implantable composition may be used in any suitable application. In some embodiments, the implantable composition may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g., edentulous patients), beneath trauma plates, tibial plateau defects, filling bone cysts, wound healing, around trauma, contouring (cosmetic/plastic/reconstructive surgery), and others. The implantable composition may be used in a minimally invasive procedure via placement through a small incision, delivery through a tube, or other means. The size and shape may be designed with restrictions on delivery conditions.

In some embodiments, the implantable composition is flexible enough so that it can be folded upon itself before it is implanted at, near, or in the bone defect.

An exemplary application for using an implantable composition as disclosed is fusion of the spine. In clinical use, the implantable composition and delivered substance may be used to bridge the gap between the transverse processes of adjacent or sequential vertebral bodies. The implantable composition may be used to bridge two or more spinal motion segments. The implantable composition surrounds the substance to be implanted, and contains the substance to provide a focus for healing activity in the body.

Generally, the implantable composition may be applied to a pre-existing defect, to a created channel, or to a modified defect. Thus, for example, a channel may be formed in a bone, or a pre-existing defect may be cut to form a channel, for receipt of the device. The implantable composition may be configured to match the channel or defect. In some embodiments, the configuration of the implantable composition may be chosen to match the channel. In other embodiments, the channel may be created, or the defect expanded or altered, to reflect a configuration of the implantable composition. The implantable composition may be placed in the defect or channel and, optionally, coupled using attachment mechanisms. In some embodiments, the implantable composition comprises a coherent mass comprising moldable entangled fibers. In some embodiments, the moldable entangled fibers are placed in the patient's defect using fingers or other medical instruments such that the moldable entangled fibers are mixed and shaped in situ to conform with the desired implant site in the patient. In some embodiments, the implantable composition comprises patient bone (autograft) prior to the placement into the patient's defect.

Printing Material

In various embodiments, the implantable composition made by a 3-D printing device may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the printing material may be braided.

In certain embodiments, a bone void can be filled by fibers containing bone material and/or a bone repair substance.

Suitable adhesives for use with the fiber may include, for example, cyanoacrylates (such as histoacryl, B Braun, which is n-butyl-2 cyanoacrylate; or Dermabond, which is 2-octylcyanoacrylate), epoxy-based compounds, dental resin sealants, dental resin cements, glass ionotner cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, for example, for fixation during the surgical procedure and for a limited time thereafter, while in other circumstances a permanent adhesive may be desired.

In some embodiments, the implantable composition may include a biological attachment such as mechanisms that promote tissue ingrowth, such as, for example, a porous coating or a hydroxyapatite-tricalcium phosphate (HA/TCP) coating. Generally, hydroxyapatite bonds are formed by the biological effects of new tissue formation. Porous ingrowth surfaces, such as titanium alloy materials in a beaded coating or tantalum porous metal or trabecular metal may be used and facilitate attachment at least at or nearby the implantable composition, encouraging bone to grow through the porous implant surface.

In other embodiments, suitable materials for the implantable composition include natural materials, synthetic polymeric resorbable materials, synthetic polymeric non-resorbable materials, and other materials. Natural materials include silk, extracellular matrix (such as DBM, collagen, ligament, tendon tissue, or other), silk-elastin, elastin, collagen, and cellulose. Synthetic polymeric resorbable materials include poly lactic acid) (PLA), poly(glycolic acid) (PGA), poly (lactic acid-glycolic acid) (PLGA), polydioxanone, PVA, polyurethanes, polycarbonates, and others.

In various embodiments, the implantable composition comprises a polymer matrix. In some embodiments, DBM fibers and/or DBM powder are suspended in the polymer matrix to facilitate transfer of cells into and out of the fibers to induce bone growth at the surgical site. In other embodiments, implantable composition further comprises mineralized bone fibers suspended in the polymer matrix.

Fiber materials may have functional characteristics. Alternatively, other materials having functional characteristics may be incorporated into the implantable composition. Functional characteristics may include radiopacity, bacteriocidity, source for released materials, tackiness, etc. Such characteristics may be imparted substantially throughout the implantable composition or at only certain positions or portions of the implantable composition.

Suitable radiopaque materials include, for example, ceramics, mineralized bone, ceramics/calcium phosphates/ calcium sulfates, metal particles, fibers, and iodinated polymer (see, for example, WO/2007/143698). Polymeric materials may be used to form a bone graft or a fiber and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, the implantable composition does not contain any carrier and does not require any wetting agent. In some embodiments, the implantable composition maybe formed as a coherent mass through mechanical entanglement. In some embodiments, the implantable composition may comprise a carrier material that becomes tacky upon wetting. Such material may be, for example, a protein or gelatin based material. Tissue adhesives, including mussel adhesive proteins and cryanocrylates, may be used to impart tackiness to the implantable composition. In further examples, alginate or chitosan material may be used to impart tackiness to the implantable composition. In further embodiments, an adhesive substance or material may be placed on a portion of the implantable composition or in a particular region of the implantable composition to anchor that portion or region of the implantable composition in place at an implant site.

In various embodiments, for example, the implantable composition made by a 3-D printing device includes a fiber to hold osteogenic material, such as bone material. In various embodiments, the bone material may be particulated, such as, for example, in bone chip, powder or fiber form. If the bone is demineralized, the bone may be made into a particulate before, during or after demineralization. In some embodiments, the bone may be monolithic and may not be a particulate. In some embodiments, the bone materials are incorporated with the biodegradable polymer as the printing material for printing the fibers.

Bone used in the methods and the implant described herein may be autograft, allograft, or xenograft. In various embodiments, the bone may be cortical bone, cancellous bone, or cortico-cancellous hone. While specific discussion is made herein to demineralized bone matrix, hone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (Including a cadaver) of the same species (allograft bone).

In some embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the fibers can have an average length from about 4.0 cm to about 6.0 cm and an average width from about 20 mm to about 1 cm.

In yet other embodiments, the diameter or average width of the fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1, or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the fibers have a thickness of about 0.5-4 mm. In various embodiments, the fibers have a thickness of about 0.01, 0.05, 0.1, 0.25, 0.5, 0.6, 0.7, 0.8, 0.9, 1, 1.5, 2, 2.5, 3, 3.5 and/or 4 mm. In various embodiments, the fibers have a diameter of about 0.01, 0.05, 0.1, 0.25, 0.5, 0.6, 0.7, 0.8, 0.9, 1, 1.5, 2, 2.5, 3, 3.5 and/or 4 mm. The fibers may have bone material in the fiber, which can be in the ink when the fiber is printed or disposed on the fiber, for example, with adhesive or while the fiber is printed.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

Microspheres

In some embodiments, the bioactive agent included in the fiber may be entrapped in a microsphere or polymer beads prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

In certain implementations, the microspheres incorporated into the fiber are from about 1 μm to about 750 μm diameter in size. In other implementations the microspheres can vary from about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, to about 750 μm diameter in size. In yet other aspects, the microspheres are porous and comprise pores having a size from about 1 μm to about 100 μm. By adding a known amount of bioactive agent to the microspheres or polymer beads present in the carrier material or fiber during the formation of the implantable composition by 3-D printing, it is possible to control the delivery mechanism of the bioactive agent from the implantable composition in a graded fashion preventing too much of the bioactive agent to be released all at once.

In other aspects, a 3-D printer can prepare an implantable composition by combining a carrier material containing microspheres including bioactive agents and a bone material to form the fiber, wherein the implantable composition is printed on a substrate that, has load bearing strength, for example, a biocompatible or biodegradable metal or other non-metallic graft. In various aspects, the microspheres of the carrier material can include additional additives, for example, drugs, growth factors, proteins or a combination thereof.

Curable Ink in several implementations, the carrier material comprises an ink that dries, is cured or reacts to form a porous, biodegradable, biocompatible material that is osteoinductive and has a load bearing strength comparable to bone. The ink can, in some aspects, be supplied in the form of a precursor powder and a precursor liquid. These may be fed to separate containers in the 3-D printer. Prior to printing, a quantity of the precursor powder and the precursor liquid may be mixed to form the ink to be used for printing the implantable composition. The printing may be accomplished by delivering quantities of the ink via a suitably sized print nozzle that may be moved in a raster scan with respect to the implantable composition being printed.

The precursor powder of the ink can contain a variety of ingredients such as, but not limited to, demineralized allograft bone matrix (DBM), a radical polymerization initiator, for example, dibenzoyl peroxide or some combination thereof. The precursor liquid may contain a variety of ingredients such as, for example, methyl methacrylate (MMA), a radiopaque compound, an antibiotic, and a compound to increase the biodegradability, or a combination thereof in some aspects, a radiopaque compound can be, without limitations, zirconium dioxide or barium sulfate or a combination thereof. In other aspects, useful antibiotics include without limitation amoxicillin, doxycycline, gentamicin, clindamycin or a combination thereof. Other additives which may increase the biodegradability of the ink include, without limitation, cellulose acetate (CA), cellulose acetate phthalate (CAP) or a combination thereof.

In alternate embodiments, the ink may include synthetic bone substitutes, and other slow reabsorbing biocompatible, bioactive adhesives as discussed above. Examples of artificial bone substitutes include without limitation hydroxyapatite, synthetic calcium phosphate ceramic or a combination thereof. These may be used instead of, or with natural bone particulates such as, without limitation, allograft, fully demineralized bone fibers and surface demineralized bone chips, or a combination thereof. These may be used with synthetically produced bone morphogenetic agents such as, without limitation, recombinant human bone morphogenetic protein rhBMP-2. Alternative inks may also include other biocompatible, bioactive adhesives such as, for example, glass polyalkenoate cements, oleic methyl ester based adhesives, or a combination thereof.

In accordance with other embodiments, the carrier material used to make the fiber may be supplemented with other microparticles and/or nanoparticles which can be incorporated before or during 3-D printing in order to impart certain desirable mechanical, magnetic, piezoelectric properties and/or stimulate cellular functions upon implantation under a variety of in vivo or in vitro conditions to the implantable composition described in this disclosure.

Sterilization of the Implantable Composition

In various aspects, the implantable composition obtained by the methods of this application can be terminally sterilized as they are formed, during the curing process or in the final packaging step. In various embodiments, one or more components of the implant may be sterilizable by radiation in a terminal sterilization step in the final packaging. Terminal sterilization of a product provides greater assurance of sterility than from processes such as aseptic processes, which require individual product components to be sterilized separately and the final package assembled in a sterile environment.

In various embodiments, gamma radiation is used in the terminal sterilization step, which involves utilizing ionizing energy from gamma rays that penetrate deeply into the implant. Gamma rays are highly effective in killing microorganisms; they leave no residues nor have sufficient energy to impart radioactivity to the bone graft. Gamma rays can be employed when the bone graft is in the package and gamma sterilization does not require high pressures or vacuum conditions, thus, package seals and other components are not stressed. In addition, gamma radiation eliminates the need for permeable packaging materials.

In some embodiments, the bone graft may be packaged in a moisture resistant package and then terminally sterilized by gamma irradiation. In use, the surgeon removes one or all components from the sterile package for use.

In various embodiments, electron beam (e-beam) radiation may be used to sterilize one or more components of the bone graft. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implant and/or one or more components of the implant, including, but not limited to, gas sterilization, such as, for example, with ethylene oxide or steam sterilization.

Composite Ink

In various embodiments, an ink for use with a 3-D printer system described herein is a composite ink. In some aspects, the 3-D printer can use as ink a composite filament comprising a polymer and chips, microparticles, nanoparticles and/or fibers of demineralized bone, non-demineralized bone or a combination thereof. In some embodiments, the composite filament comprises a bioerodible polymer, one or more ceramics and demineralized bone matrix (DBM) where the demineralized bone matrix particles are embedded within or coated on the surface of the bioerodible polymer and ceramic particles. In a further embodiment, the demineralized bone matrix particles are dispersed throughout the bioerodible polymer and ceramic particles. In some embodiments, the demineralized bone matrix particles are dispersed homogeneously throughout the polymer and ceramic particles.

In some embodiments, the composite ink used to make the fiber comprises a bioerodible polymer that will exhibit dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation.

In some embodiments, hydrophobic polymers (e.g., poly (lactide-co-glycolyde), polyanhydrides) may be used. Alternatively, a combination of hydrophilic and hydrophobic polymers may be used in the implantable composition of the disclosure.

Exemplary materials may include biopolymers and synthetic polymers such as human skin, human hair, bone, collagen, fat, thin cross-linked sheets containing fibers and/ or fibers and chips, polyethylene glycol (PEG), chitosan, alginate sheets, cellulose sheets, hyaluronic acid sheets, as well as copolymer blends of poly (lactide-co-glycolide) PLGA.

In some embodiments, the particles disclosed herein can also include other biocompatible and bioresorbable substances. These materials may include, for example, natural polymers such as proteins and polypeptides, glycosaminoglycans, proteoglycans, elastin, hyaluronic acid, dermatan sulfate, gelatin, or mixtures or composites thereof. Synthetic polymers may also be incorporated into the implantable composition composites. These include, for example biodegradable synthetic polymers such as polylactic acid, polyglycolide, polylactic polyglycolic acid copolymers ("PLGA"), polycaprolactone ("PCL"), poly(dioxanone), poly(trimnethylene carbonate) copolymers, polyglyconate, poly(propylene fumarate), poly(ethylene terephthalate), poly(butylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, that can be polymerized from the monomers related to previously-listed homo- and copolymers.

In some embodiments, the bioerodible polymer is collagen. Collagen has excellent histocompatibility without antibody formation or graft rejection. Any suitable collagen material may be used, including known collagen materials, or collagen materials as disclosed in U.S. patent application Ser. No. 12/030,181, filed Feb. 12, 2008, hereby incorporated by reference in its entirety. Various collagen materials can be used, alone or in combination with other materials.

Insoluble collagen material for use in the disclosure can be derived from natural tissue sources, (e.g., xenogenic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen and may be used in the present disclosure, Type I collagen is present in skin, tendon and bone, whereas Type III collagen is found primarily in skin. The collagen used in compositions of the disclosure can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Kensey Nash Corporation (Exton, Pa.), which manufactures a fibrous collagen known as Seined from bovine hides. Collagen materials derived from bovine hide are also manufactured by Integra Life Science Holding Corporation (Plainsboro, N.J.). Naturally-derived or recombinant human collagen materials are also suitable for use in the disclosure. Illustratively, recombinant human collagen products are available from Fibrogen, Inc. (San Francisco, Calif.).

The solid particulate collagen incorporated into the inventive compositions can be in the form of intact or reconstituted fibers, or randomly-shaped particles, for example. In certain embodiments, the solid particulate collagen will be in the form of particles derived from a sponge material, for example by randomly fragmenting the sponge material by milling, shredding or other similar operations. Such particulated sponge material can have an average maximum particle diameter of less than about 6 mm, less than about 3 mm, or in the range of about 0.5 mm to 2 mm. Such materials can, for example, be obtained by milling or grinding a porous sponge material and sieving the milled or ground material through a screen having openings sized about 6 mm or smaller, or about 0.5 mm to about 2 mm. Retch grinders with associated sieves are suitable for these purposes. Other sources of chemically crosslinked, particulate collagen, in fiber, irregular or other shapes, can also be used, and their use is considered to be another aspect of the present disclosure. These crosslinked particulate materials can be provided as starting materials for preparing composite compositions as disclosed herein, and therefore as incorporated in the implantable composition, these particles are individually crosslinked. Crosslinked solid collagen particles can be used in combination with non-crosslinked collagen in compositions of the disclosure, wherein the non-crosslinked collagen can be solid (insoluble) or soluble collagen, or combinations thereof. Such crosslinked and non-crosslinked collagen mixtures can be used, for example, to modulate the residence time of the collagen portion of the implantable composition in vivo.

Suitable crosslinking agents include, but are not limited to, mono- and dialdehydes, including glutaraldehyde and formaldehyde; polyepoxy compounds such as glycerol; and sugars such as glucose. In one embodiment, the crosslinking agent is glycerol.

Exemplary collagen particles can be obtained from various collagen sources including human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is porous.

In some embodiments, the bioerodible polymer may be hyaluronic acid, chitosan, chitin, keratin, cellulose, glycosaminoglycans and derivatives thereof (e.g. esters of hyaluronic acid) or others of synthetic origin which may be used as an alternative to or in combination with collagen.

In some embodiments, the synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP).

Biphasic calcium phosphate can have a tricalcium phosphate:hydroxyapatite weight ratio of about 50:50 to about 95:5, about 70:30 to about 95:5, about 80:20 to about 90:10, or about 85:15. The mineral material can be a granular particulate having an average particle diameter between about 0.2 and 5.0 mm, between about 0.4 and 3.0 mm, or between about 0.4 and 2.0 mm.

The ceramics of the disclosure may also be oxide ceramics such as alumina ($Al_2O_3$) or zirconia ($ZrO_2$) or composite combinations of oxides and non-oxides such as silicon nitride.

The ceramics of the disclosure may be porous and may have pore sizes large enough to permit osteoinduction via invasion of the material by bone forming cells. Examples of porous ceramics are hydroxyapatite and TCP.

In some embodiments, the non-allograft bone material that can be used in the fiber includes from about 40 to about 60 weight percent collagen, from about 20 to about 50 weight percent DBM, and from about 10 to about 50 weight percent ceramics. In some embodiments, the ratio of DBM particles to collagen and/or ceramics is about 5:1, about 4:1, about 3:1, about 2:1, about 1:1, about 1:5, about 1:4, about 1:3, or about 1:2, In some embodiments, the ratio of DBM particles to collagen and/or ceramics is about 1.5:0.5, about 1:1, or about 0.5:1.5.

In some embodiments, the particles disclosed herein that can be used in the fiber also include synthetic ceramics that are effective to provide a scaffold for bone growth and which are completely bioresorbable and biocompatible. The synthetic ceramics should provide high local concentrations of calcium, phosphate and silicon ions that act as a nidus for de-novo bone formation. The use of such resorbable ceramics provides many advantages over alternative conventional materials. For instance, it eliminates the need for post-therapy surgery for removal and degrades in the human body to biocompatible, bioresorbable products.

In other embodiments, the composite filament for use in a 3-D printer system described herein is a curable composite ink. The composite ink comprises a curable material and, optionally a colorant dispersed in the ink, in amount from about 0.01 to about 5% by weight of the composite ink. In some cases, the colorant is present in the composite ink in an amount between about 0.01 and 3 weight %; between about 0.01 and 1 weight %, between about 0.05 and 5 weight %, between about 0.05 and 3 weight %, between about 0.05 and 1 weight %, between about 0.1 and 5 weight %, between about 0.1 and 3 weight %, or between about 0.1 and 1 weight %. In some aspects, the colorant of a composite ink comprises an inorganic pigment, such as $TiO_2$ and ZnO. In some embodiments, the colorant of a composite ink comprises a colorant for use in a KGB, sRGB, CMY, CMYK, L*a*b*, or Pantone® colorization scheme. Moreover, in some cases, a particulate colorant described herein has an average particle size of less than 500 nm, such as an average particle size of less than 400 nm, less than 300 nm, less than 250 nm, less than 200 nm, or less than 150 nm. In some instances, a particulate colorant has an average particle size of 50-1000 nm, 50-500 am, 50-400 nm, 50-300 nm, 50-200 nm, 70-500 nm, 70-300 nm, 70-250 nm, or 70-200 nm.

In certain embodiments, the curable material included in the composite filament is present in an amount up to about 99 weight %, up to about 95 weight %, up to about 90 weight %, or up to about 80 weight %, based on the total weight of the composite ink. In some cases, a composite ink described herein comprises about 10-95 weight % curable material based on the total weight of the carrier ink. In some embodiments, a carrier ink comprises about 20-80 weight % curable material, about 30-70 weight % curable material, or about 70-90 weight % curable material.

In some cases, a curable material comprises one or more polymerizable components. As used herein, a polymerizable component comprises a component that can be polymerized or cured to provide a 3-D printed article or object. In some embodiments, polymerizing or curing comprises irradiating with electromagnetic radiation having sufficient energy to initiate a polymerization or cross-linking reaction. In other embodiments, ultraviolet (IN) radiation can be used.

In some embodiments, a polymerizable component comprises a monomeric chemical species, such as a chemical species having one or more functional groups or moieties that can react with the same or different functional groups or moieties of another monomeric chemical species to form one or more covalent bonds, such as in a polymerization reaction. A polymerization reaction, in some embodiments, comprises a free radical polymerization, such as that between points of unsaturation, including points of ethylenic unsaturation. In some embodiments, a polymerizable component comprises at least one ethylenically unsaturated moiety, such as a vinyl group or allyl group. In some embodiments, a polymerizable component comprises an oligomeric chemical species capable of undergoing additional polymerization, such as through one or more points of unsaturation as described herein. In other embodiments, a polymerizable component comprises one or more monomeric chemical species and one or more oligomeric chemical species as described herein. A monomeric chemical species and/or an oligomeric chemical species described herein can have one polymerizable moiety or a plurality of polymerizable moieties.

In some embodiments, a polymerizable component comprises one or more photo-polymerizable or photo-curable chemical species. A photo-polymerizable chemical species, in some embodiments, comprises a UV-polymerizable chemical species. In some embodiments, a polymerizable component is photo-polymerizable or photo-curable at wavelengths ranging from about 300 nm to about 400 nm. Alternatively, in some embodiments, a polymerizable component is photo-polymerizable at visible wavelengths of the electromagnetic spectrum.

In some embodiments, a polymerizable component described herein comprises one or more species of (meth) acrylates including acrylate or methacrylate or mixtures or combinations thereof. In other embodiments, a polymerizable component comprises an aliphatic polyester urethane acrylate oligomer, a urethane (meth)acrylate resin, and/or an acrylate amine oligomeric resin, such as EBECRYL 7100. In yet other embodiments, a UV polymerizable or curable resin or oligomer can comprise any methacrylate or acrylate resin which polymerizes in the presence of a free radical photoinitiator, is thermally stable in an exposed state for at least one week at a jetting temperature and for at least 4 weeks in an enclosed state, and/or has a boiling point greater than the jetting temperature. In some embodiments, a polymerizable component has a flash point above the jetting temperature.

Urethane (meth)acrylates suitable for use in inks described herein, in some embodiments, can be prepared in a known manner, typically by reacting a hydroxyl-terminated urethane with acrylic acid or methacrylic acid to give the corresponding urethane (meth)acrylate, or by reacting an isocyanate-terminated prepolymer with hydroxyalkyl acrylates or methacrylates to give the urethane (meth)acrylate. The weight average molecular weight of such (meth)acrylate oligomers is generally in the range from about 400 to 10,000, or from about 500 to 7,000. Urethane (meth)acrylates are commercially available from the SARTOMER Company under the product names CN980, CN981, CN975 and CN2901, or from Bomar Specialties Co. (Winsted, Conn.) under the product name BR-741. In some embodiments, a urethane (meth)acrylate oligomer has a viscosity ranging from about 140,000 cP to about 160,000 cP at about 50° C. or from about 125,000 cP to about 175,000 cP at about 50° C. when measured in a manner consistent with ASTM D2983, In some embodiments described herein, a urethane (meth)acrylate oligomer has a viscosity ranging from about 100,000 cP to about 200,000 cP at about 50° C. or from about 10,000 cP to about 300,000 cP at about 50° C. when measured in a manner consistent with ASTM D2983.

In various embodiments, a polymerizable component comprises one or more low molecular weight materials, such as methacrylates, dimethacrylates, triacrylates, and diacrylates, which can be used in a variety of combinations. In some embodiments, for example, a polymerizable component comprises one or more of tetrahydrofurfuryl methacrylate, triethylene glycol dimethacrylate, 2-phenoxyethyl methacrylate, lauryl methacrylate, ethoxylated trimethylolpropane triacrylate, tricyclodecane dimethanol diacrylate, 2-phenoxyethylacrylate, triethylene glycol diacrylate, a monofunctional aliphatic urethane acrylate, polypropylene glycol monomethacrylate, polyethylene glycol monomethacrylate, cyclohexane dimethanol diacrylate, and tridecyl methacrylate.

In some embodiments, a polymerizable component comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis (4-hydroxy cyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S.

A polymerizable component, in some embodiments, comprises one or more tri(meth)acrylates. In some embodiments, tri(meth)acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate.

In other embodiments, a polymerizable component of the composite filament described herein comprises one or more higher functional acrylates or methacrylates such as dipentaerythritol monohydroxy pentaacrylate or bis(trimethylolpropane) tetraacrylate. In some embodiments, a (meth) acrylate of an ink has a molecular weight ranging from about 250 to 700.

In certain embodiments, a polymerizable component comprises allyl acrylate, allyl methacrylate, methyl (meth) acrylate, ethyl (meth)acrylate, n-propyl (meth)acrylate, n-butyl (meth)acrylate, isobutyl (meth)acrylate, n-hexyl (meth)acrylate, 2-ethylhexyl (meth)acrylate, n-octyl (meth) acrylate, n-decyl (meth)acrylate and n-dodecyl (meth)acrylate, 2-hydroxyethyl (meth)acrylate, 2- and 3-hydroxypropyl (meth)acrylate, 2-methoxyethyl(meth)acrylate, 2-ethoxyethyl (meth)acrylate and 2- or 3-ethoxypropy (meth)acrylate, tetrahydrofurfuryl methacrylate, 2-(2-ethoxyethoxyl) ethyl acrylate, cyclohexyl methacrylate, 2-phenoxyethyl acrylate, glycidyl acrylate, isodecyl acrylate, or a combination thereof.

Additional non-limiting examples of species of polymerizable components useful in some embodiments described herein include the following: isobornyl acrylate (IBOA), commercially available from SARTOMER under the trade name SR 506A; isobornyl methacrylate, commercially available from SARTOMER under the trade name SR 423A; alkoxylated tetrahydrofurfuryl acrylate, commercially available from SARTOMER under the trade name SR 611; monofunctional urethane acrylate, commercially available from RAHN USA under the trade name GENOMER 1122; aliphatic urethane diacrylate, commercially available from ALLNEX under the trade name EBECRYL 8402; triethylene glycol diacrylate, commercially available from SARTOMER under the trade name SR 272; triethylene glycol dimethacrylate, commercially available from SARTOMER under the trade name SR 205; tricyclodecane dimethanol diacrylate, commercially available from SARTOMER under the trade name SR 8335; tris(2-hydroxy ethyl)isocyanurate triacrylate, commercially available from SARTOMER under the trade name SR 368; and 2-phenoxyethyl acrylate, commercially available from SARTOMER under the trade name SR 339, Other commercially available curable materials may also be used.

The composite filament ink that can be used to make the fiber described in this disclosure can also include one or more additives selected from the group consisting of photoinitiators, inhibitors, stabilizing agents, sensitizers, and combinations thereof. In some embodiments, suitable photoinitiators comprise benzoins, including benzoin, benzoin ethers, such as benzoin methyl ether, benzoin ethyl ether and benzoin isopropyl ether, benzoin phenyl ether and benzoin acetate, acetophenones, including acetophenone, 2,2-dimethoxyacetophenone and 1,1-dichloroacetophenone, benzil, benzil ketals, such as benzil dimethyl ketal and benzil diethyl ketal, anthraquinones, including 2-methylanthraquinone, 2-ethylanthraquinone, 2-tert-butylanthraquinone, 1-chloroanthraquinone and 2-amylanthraquinone, triphenyl) phosphine, benzoylphosphine oxides, for example 2,4,6-trimethylbenzoyldiphenylphosphine oxide (Lucirin TPO), benzophenones, such as benzophenone and 4,4'-bis(N,N'-dimethylamino)benzophenone, thioxanthenes and xanthenes, acridine derivatives, phenazine derivatives, quinoxaline derivatives or 1-phenyl-1,2-propanedione, 2-O-benzoyl oxime, 1-aminophenyl ketones or 1-hydroxyphenyl ketones, such as 1-hydroxycyclohexyl phenyl ketone, phenyl 1-hydroxyisopropyl ketone and 4-isopropylphenyl 1-hydroxyisopropyl ketone.

In some cases, suitable photoinitiators comprise those operable for use with a HeCd laser radiation source, including acetophenones, 2,2-di alkoxybenzophenones and 1-hydroxyphenyl ketones, such as 1-hydroxycyclohexyl phenyl ketone or 2-hydroxyisopropyl phenyl ketone hydroxy-2,2-dimethylacetophenone). Additionally, in other aspects, suitable photoinitiators comprise those operable for use with an Ar laser radiation source including benzil ketals, such as benzil dimethyl ketal. In some embodiments, a photoinitiator comprises an α-hydroxyphenyl ketone, benzil dimethyl ketal or 2,4,6-trimethylbenzoyldiphenylphosphine oxide or a mixture thereof.

Other suitable photoinitiators comprise ionic dye-counter ion compounds capable of absorbing actinic radiation and generating free radicals for polymerization initiation. In some embodiments, inks containing ionic dye-counter ion compounds can be cured more variably with visible light within the adjustable wavelength range of about 400 nm to about 700 nm.

A photoinitiator can be present in an ink described herein in any amount not inconsistent with the objectives of the present disclosure. In some embodiments, a photoinitiator is present in an ink in an amount of up to about 5 weight percent, based on the total weight of the ink. In some embodiments, a photoinitiator is present in an amount ranging from about 0.1 weight percent to about 5 weight percent.

In some embodiments, a method of printing a 3-D implantable composition comprises selectively depositing layers of a composite ink described herein in a fluid state onto a substrate to form the fiber. For example, in some cases, the composite filament ink comprises a curable material and a colorant dispersed in the curable material in an amount of about 0.01 to 5 weight %, based on the total weight of the composite ink. Further, the layers of a composite filament ink can be deposited according to an image of the 3-D implantable composition in a computer readable format. In some embodiments, the ink is deposited according to preselected computer aided design (CAD) parameters on to a metal or non-metal substrate.

Moreover, in some cases, one or more layers of a composite ink described herein have a thickness of about 0.03 to about 5 mm, a thickness of about 0.03 to about 3 mm, a thickness of about 0.03 to about 1 mm, a thickness of about 0.03 to about 0.5 mm, a thickness of about 0.03 to about 0.3 mm, a thickness of about 0.03 to about 0.2 mm, a thickness of about 0.05 to about 5 mm, a thickness of about 0.05 to about 1 mm, a thickness of about 0.05 to about 0.5 mm, a thickness of about 0.05 to about 0.3 mm, or a thickness of about 0.05 to about 0.2 mm. Other thicknesses are also possible.

A method described herein can also comprise curing the layers of the composite ink. In some embodiments, a method of printing an implantable composition further comprises subjecting the ink to electromagnetic radiation of sufficient wavelength and intensity to cure the ink, where curing can comprise polymerizing one or more polymetizable functional groups of one or more components of the ink. In some embodiments of printing a 3-D implantable composition, a layer of deposited ink is cured prior to the deposition of another or adjacent layer of ink.

In some embodiments, a preselected amount of ink described herein is heated to the appropriate temperature and jetted through the print head or a plurality of print heads of a suitable inkjet printer to form a layer on a print pad in a print chamber. In some embodiments, each layer of ink is deposited according to the preselected CAD parameters. A suitable print head to deposit the ink, in some embodiments, is a piezoelectric print head. Additional suitable print heads for the deposition of ink and support material described herein are commercially available from a variety of ink jet printing apparatus manufacturers. For example, Xerox, Hewlett Packard, or Ricoh print heads may also be used in some instances.

In some embodiments, a method of printing a 3-D article comprises using a composite ink, wherein the composite ink remains substantially fluid upon deposition. In other embodiments, the ink exhibits a phase change upon deposition and/or solidifies upon deposition. In some embodiments, the temperature of the printing environment can be controlled so that the jetted droplets of ink solidify on contact with the receiving surface. In other embodiments, the jetted droplets of ink do not solidify on contact with the receiving surface, remaining in a substantially, fluid state. In some embodiments, after each layer is deposited, the deposited material is planarized and cured with electromagnetic (e.g., UV) radiation prior to the deposition of the next layer. Optionally, several layers can be deposited before planarization and curing, or multiple layers can be deposited and cured followed by one or more layers being deposited and then planarized without curing. Planarization corrects the thickness of one or more layers prior to curing the material by evening the dispensed material to remove excess material and create a uniformly smooth exposed or flat up-facing surface on the support platform of the printer.

In another embodiment, mechanical, magnetic, and/or piezoelectric sensitive micro-, nanoparticles or patterns are incorporated during 3-D printing to stimulate cellular functions upon implantation under a variety of in vivo or in vitro mechanical, magnetic or pressure conditions.

Layered 3-D Printed Implantable Composition

In certain embodiments, the computer implemented method described herein provides a layered 3-D printed implantable composition. In some implementations, the 3-D printed implantable composition includes a coherent mass comprising the fibers comprising a biodegradable polymer and/or bone material binding mechanically among the fibers themselves. In some embodiments, the fibers form multiple layers that can be formed into a coherent mass.

As discussed above in connection with the computer implemented method for producing the implantable composition of this disclosure, in some embodiments, the bone material of the implantable composition comprises (i) mineralized allograft and non-demineralized allograft or a combination thereof; or (ii) allograft, demineralized bone matrix fiber and demineralized bone chips or a combination thereof. In other embodiments, the 3-D printed implantable composition contains bone material which comprises (i) fully demineralized bone fibers and surface demineralized bone chips, or (ii) a demineralized bone matrix material comprising fully demineralized bone matrix fibers and surface demineralized bone chips in a ratio of from about 25:75 to about 75:25.

In various embodiments, as described above, the polymer of the carrier material comprises a curable biocompatible and/or biodegradable polymer. In these embodiments, the biodegradable polymer comprises at least one of polylactic acid), poly(glycolic acid), poly(lactic acid-glycolic acid), polydioxanone, PVA, polyurethanes, polycarbonates, polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, polyglycolide-co-tri methylene carbonate, poly(lactic-co-glycolic acid) or combinations thereof. In other embodiments, the biodegradable polymer further comprises at least one of a polymer sugar, protein, hydrophilic block copolymer, hyaluronic acid, polyuronic acid, mucopolysaccharide, proteoglycan, polyoxyethylene, surfactant, polyhydroxy compound, polyhydroxy ester, fatty alcohol, fatty alcohol ester, fatty acid, fatty acid ester, liquid silicone, or combinations thereof.

In some uses, the carrier acts as a temporary scaffold until replaced by new bone. Polylactic acid (PLA), polyglycolic acid (PGA), and various combinations have different dissolution rates in vivo. In bone, the dissolution rates can vary according to where the bone allograft is placed.

Although the invention has been described with reference to certain embodiments, persons skilled in the art will recognize that changes may be made in form and detail without departing from the spirit and scope of the invention.

What is claimed is:

1. An implantable composition comprising a first set of fibers and a second set of fibers, the first set of fibers manufactured to have a first binding surface, the second set of fibers manufactured to have a second binding surface, the first binding surface of the first set of fibers configured to bind at least at or near the second binding surface of the second set of fibers and the second set of fibers configured to bind at least at or near the first binding surface of the first set of fibers, wherein the first binding surface of the first set of fibers comprises a curl portion, a helical portion, a spiral portion, a twist portion or a ribbon portion and the second binding surface of the second set of fibers also comprises a curl portion, a helical portion, a spiral portion, a twist portion or a ribbon portion, and wherein the first set of fibers comprises a body portion and an end portion such that the first binding surface of the first set of fibers is disposed near the end portion.

2. The implantable composition according to claim 1, wherein the first set of fibers comprises a first non-binding surface and the second set of fibers comprises a second non-binding surface, wherein the first binding surface of the first set of fibers bind at least at or near the second binding surface of the second set of fibers and the second set of fibers bind at least at or near the first binding surface of the first set of fibers so as to form a coherent mass of bound first set of fibers and second set of fibers.

3. The implantable composition according to claim 1, wherein the first binding surface of the first set of fibers further comprises a hook portion, a branched portion, a barbed portion, a looped portion, a chain portion, an angular portion, a sinusoidal portion, or a zigzag portion and the second binding surface of the second set of fibers also further comprises a hook portion, a branched portion, a barbed portion, a looped portion, a chain portion, a spiral portion, an angular portion, a sinusoidal portion, or a zigzag portion.

4. The implantable composition according to claim 2, wherein the first non-binding surface of the first set of fibers comprises a straight portion and the second non-binding surface of the second set of fibers also comprises a straight portion and the implantable composition is a bone void filler.

5. The implantable composition according to claim 1, wherein the first set of fibers and the second set of fibers comprise a resorbable polymer, a non-resorbable polymer, an ink of organic material, an ink of synthetic material, a therapeutic agent, a soft tissue, a bone material or a combination thereof.

6. The implantable composition according to claim 1, wherein the first set of fibers and the second set of fibers are made by additive manufacturing, stereolithography, extrusion molding, ultraviolet light printing or a combination thereof.

7. A computer implemented method for producing an implantable composition of claim 1, the method comprising generating a 3-D digital model of the implantable composition, the 3-D digital model being of a first set of fibers and a second set of fibers, the first set of fibers comprising a first binding surface, the second set of fibers comprising a second binding surface, the first binding surface of the first set of fibers configured to bind at least at or near the second binding surface of the second set of fibers and the second set of fibers configured to bind at least at or near the first binding surface of the first set of fibers; and storing the 3-D digital model on a database coupled to a processor, the processor having instructions for selecting the implant material based on the stored 3-D digital model and for instructing a print surface of a 3-D printer to print the implantable composition on the print surface.

8. The computer implemented method of claim 7, wherein the first binding surface of the first set of fibers further comprises a hook portion, a branched portion, a barbed portion, a looped portion, a chain portion, an angular portion, a sinusoidal portion, or a zigzag portion and the second binding surface of the second set of fibers also further comprises a hook portion, a branched portion, a barbed portion, a looped portion, a chain portion, an angular portion, a sinusoidal portion, or a zigzag portion.

9. The computer implemented method of claim 7, wherein the first set of fibers comprises a first non-binding surface and the second set of fibers comprises a second non-binding surface.

10. The computer implemented method according to claim 7, wherein the first set of fibers and the second set of fibers comprise a resorbable polymer, a non-resorbable polymer, an ink of organic material, an ink of synthetic material, a therapeutic agent, a soft tissue, a bone material or a combination thereof, wherein the first set of fibers and the second set of fibers comprise bone material disposed in or on the fibers.

11. The computer implemented method according to claim 9, wherein the first non-binding surface of the first set of fibers comprises a straight portion and the second non-binding surface of the second set of fibers also comprises a straight portion and the implantable composition is a bone void filler.

12. The computer implemented method according to claim 7, wherein the first set of fibers and the second set of fibers are configured to be molded into a putty, paste or are configured to be lyophilized.

13. The computer implemented method according to claim 7, wherein before the 3-D digital model of the implantable composition is generated, a 3-D digital model of an intended tissue repair site is generated, and the 3-D digital model of the implantable composition is generated to fit within the 3-D digital model of the tissue repair site.

14. The computer implemented method according to claim 7, wherein before the 3-D digital model of the implantable composition is generated, a type of material that the 3-D digital model of the implantable composition is made from is selected.

15. A method of treating a bone or soft tissue defect, the method comprising inserting an implantable composition into the bone or soft tissue defect, the implantable composition comprising a first set of fibers and a second set of fibers, the first set of fibers manufactured to have a first binding surface, the second set of fibers manufactured to have a second binding surface, the first binding surface of the first set of fibers bound to at least at or near the second binding surface of the second set of fibers and the second set of fibers bound to at least at or near the first binding surface of the first set of fibers, wherein the first binding surface of the first set of fibers comprises a curl portion, a helical portion, a spiral portion, a twist portion or a ribbon portion and the second binding surface of the second set of fibers also comprises a curl portion, a helical portion, a spiral portion, a twist portion or a ribbon portion, and wherein the first set of fibers comprises a body portion and an end portion such that the first binding surface of the first set of fibers is disposed near the end portion.

16. The method of treating according to claim 15, wherein the first binding surface of the first set of fibers further comprises a hook portion, a branched portion, a barbed portion, a looped portion, a chain portion, an angular portion, a sinusoidal portion, or a zigzag portion and the second binding surface of the second set of fibers also further comprises a hook portion, a branched portion, a barbed portion, a looped portion, a chain portion, an angular portion, a sinusoidal portion, or a zigzag portion.

17. The method of treating according to claim 15, wherein the first set of fibers comprises a first non-binding surface and the second set of fibers comprises a second non-binding surface, and the implantable composition is a bone void filler.

18. The method of treating according to claim 15, wherein the first set of fibers and the second set of fibers comprise a resorbable polymer, a non-resorbable polymer, an ink of organic material, an ink of synthetic material, a therapeutic agent, a soft tissue, a bone material or a combination thereof.

* * * * *